United States Patent
Heilbrunn et al.

(10) Patent No.: US 7,979,383 B2
(45) Date of Patent: Jul. 12, 2011

(54) ATLAS REPORTING

(75) Inventors: Ken Steven Heilbrunn, Seattle, WA (US); George Andrew Miller, Seattle, WA (US)

(73) Assignee: Atlas Reporting, LLC, Seattle, WA (US)

( * ) Notice: Subject to any disclaimer, the term of this patent is extended or adjusted under 35 U.S.C. 154(b) by 1797 days.

(21) Appl. No.: 11/146,500

(22) Filed: Jun. 6, 2005

(65) Prior Publication Data

US 2006/0277073 A1    Dec. 7, 2006

(51) Int. Cl.
G06K 00/99 (2006.01)
G06K 9/54 (2006.01)

(52) U.S. Cl. .............. 707/104.1; 382/132; 382/305; 705/3

(58) Field of Classification Search .......... 382/100, 382/128, 180, 305, 209, 171, 132, 181, 168; 705/2, 3; 704/9; 707/E17.009, E17.023, 707/999.104, 999.107; 600/300, 407, 425; 715/236, 230, 234, 205; 128/922, 920; 345/173
See application file for complete search history.

(56) References Cited

U.S. PATENT DOCUMENTS

| 4,710,876 | A | * | 12/1987 | Cline et al. | 345/423 |
| 4,729,098 | A | * | 3/1988 | Cline et al. | 345/421 |
| 5,625,354 | A | * | 4/1997 | Lerman | 341/20 |
| 5,987,345 | A | * | 11/1999 | Engelmann et al. | 600/407 |
| 5,987,459 | A | * | 11/1999 | Swanson et al. | 1/1 |
| 6,785,410 | B2 | * | 8/2004 | Vining et al. | 382/128 |
| 7,058,650 | B2 | * | 6/2006 | Yang et al. | 707/700 |
| 7,289,651 | B2 | * | 10/2007 | Vining et al. | 382/128 |
| 2005/0107690 | A1 | * | 5/2005 | Soejima | 600/425 |

* cited by examiner

*Primary Examiner* — Sheela C Chawan
(74) *Attorney, Agent, or Firm* — Black Lowe & Graham PLLC

(57) ABSTRACT

A method and database for generating a report of findings of at least one abnormality evident in a medical image, the medical image including at least a portion of at least one structure of the body, the method includes retrieving a figure of the at least one structure. The retrieved figure is amended to reflect an abnormality. The abnormality is sized with respect to the figure of the at least one structure. The abnormality is placed at a location on the figure of the at least one structure according to an orientation of that abnormality in the medical image to generate an amended figure representative of the medical image for inclusion in the report.

18 Claims, 15 Drawing Sheets

ATLAS REPORTING

BACKGROUND OF THE INVENTION

In current medical practice, diagnostic radiographic imaging examinations are usually ordered by clinical healthcare providers and interpreted by radiologists. A written interpretive report is generated by a radiologist and sent to the provider to convey and document the results of the examination. The interpreting radiologist, or other individual performing this function, will generally orally dictate a description and discussion of the abnormalities on the medical images, including text descriptive of his impression of the significance of those abnormalities. A transcriptionist or, in some instances, a computer with voice recognition software, will transform the spoken words of the radiologist into text. The radiologist dictates text documents to fulfill his professional responsibility and to convey the imaging examination results to the provider.

The radiologist is tasked with the mental conversion of an image to text, the text being the only conventional means of conveying, documenting, and communicating the radiologist's interpretation of the medical images. The descriptive text format and wording created for any given radiographic imaging examination in current medical practice will vary depending on the radiologist. Due to variance of the text in free text reporting, it is difficult, if possible at all, to extract statistics suitable for analyzing outcomes from current radiology reports.

Interpreting images is a visual, right brain function in which the radiologist drafts verbal reports of abnormalities against a mental backdrop of knowledge stored in association with images, both images that are learned in training and acquired through experience. Matching the medical images with anatomic diagrams (referred to henceforth as "drawings") allows the radiologist to remain in that visual, right brain function. Verbal dictation, on the other hand, a left brain language function, is tedious, linear, and tiring. Regardless of how carefully the text is formulated, it still cannot compete with a simple picture.

There is an unmet need in the art for a graphic means of generating reports of abnormalities on radiographic imaging examinations, and other kinds of medical examinations.

SUMMARY OF THE INVENTION

A method for generating a report of findings of at least one abnormality evident in a medical image, the medical image including at least a portion of at least one structure of the body, the method includes retrieving a figure of the at least one structure. The retrieved figure is amended to reflect an abnormality. The abnormality is sized with respect to the figure of the at least one structure. The abnormality is placed at a location on the figure of the at least one structure according to an orientation of that abnormality in the medical image to generate an amended figure representative of the medical image for inclusion in the report.

An embodiment of the invention allows the radiologist to formulate reports and to communicate their medical image interpretations by selecting isolated figures of abnormalities from a database and construct an anatomic drawing of the abnormalities, and descriptive text to serve as the interpretive report. Final reports may include the constructed anatomic drawings. In another embodiment, a free-text option, allows the radiologist to tailor the report with unstructured commentary. By generating reports according to a uniform format, an embodiment of the invention creates data to populate a database for statistical outcomes analysis. The anatomic drawing constructed by selections from the invention's database of drawings provides quick visual references for healthcare providers and their patients, guides radiologists in tailoring follow-up imaging examinations, and simplifies comparative assessments of sequential examinations.

An embodiment of the invention generates reports of abnormalities. The embodiment allows the radiologist to match the medical images with corresponding drawings and thereby remain in that visual, right brain function. Verbal dictation, on the other hand, a left-brain language function, is kept to a minimum, as it is tedious, linear, and tiring.

The inventive matching of drawings with abnormalities on the medical images inherently assists in medical image interpretation. Drawings representative of common abnormalities are especially useful for radiologists interpreting imaging examinations outside their areas of primary expertise. In an embodiment of the invention, a diagnostic help screen serves as an interview to provide diagnostic guidance for interpretation of less common findings.

Another embodiment interacts directly with the digitized data in the medical image, as well as the patient's electronic medical file and history. In this embodiment, the radiologist selects actual illustrative digitized images from the patient's medical image to be included with the written descriptive report. Another possible embodiment combines information from the patient's medical file with tissue properties determined by the medical imaging examination of the detected abnormality, as well as the anatomic location, to achieve greater diagnostic specificity.

To observe progress of a dynamic condition, follow-up imaging examinations lend the opportunity to assess the stability, resolution, or progression of abnormalities. In conventional medical practice, the radiologist may only accomplish the comparative findings by having both the prior text reports and the prior medical images in order to recreate a mental image of the abnormalities, and thus to determine the appropriate type of follow-up examination protocol needed to assess interval change. An embodiment of the invention allows the radiologist to accomplish this by reviewing the anatomic drawing constructed in a prior medical imaging report. The extensive information conveyed in the inventive reports with anatomic drawing can include sufficient detail to observe the progression of an abnormality without necessitating access to the prior medical images.

Another embodiment of the invention allows radiologists from distinct locations to provide reports that are generated to a common standard defined by the particular healthcare provider. The common standard is enforced by using a healthcare provider's set of textual templates that are associated with a given condition. The drawings that the radiologist selects will generate text according to the designated templates, thereby conforming to the reporting and statistical conventions of the healthcare provider.

An embodiment of the invention generates a report with anatomic drawings provided to enhance patients' understanding of their illnesses. A picture is worth a thousand words, especially medical words. Providing such visual information imparts to the patient an enhanced understanding of the patient's illness, a factor that may activate psycho-immunology factors important in the healing process.

A further embodiment of the invention standardizes reports while providing embedded coding to the report according to existing conventions, such as International Classification of Diseases ("ICD-10") coding. The ICD-10 coding system classifies morbidity for statistical purposes and for indexing of hospital records by disease and operations for data storage and retrieval. Diagnostic medical imaging is used to document and characterize disease, plan subsequent surgical and medical therapy, and assess response to treatment. The embodiment includes palettes of drawings representing abnormalities. Selection from these palettes drives an embedded code according to the ICD-10 system. The embodiment of the invention causes the same questions as are necessary for disease classification to be asked by visual matching of anatomic drawings to the medical images.

By means of such embedded coding, the radiologist may provide important epidemiological data to observing authorities such as the Centers for Disease Control. Where an unusual occurrence of a condition is observed, the immediate coding by the invention serves to alert the authorities of the condition. Optionally, the alerts may be automated such that the statistical occurrence of disease processes in a population may be monitored.

In an embodiment of the invention storage of disease codes with the anatomic drawings allows automated retrieval and documentation of disease prevalence, morbidity, and response to treatment. Creating a similar database from "free text reporting" is difficult, if not impossible. This embodiment could be used to automatically gather information comparing the effectiveness of different treatments of disease. It may provide important epidemiological data to observing authorities such as the Centers for Disease Control. Compiling data from multiple healthcare centers using the invention could improve policy decisions for research funding and healthcare money allocations. Where a surprising or unusual occurrence of a condition is observed, the immediate coding by the embedded means of an embodiment of the invention serves to alert the authorities of the condition. Optionally, the alerts may be automated such that the statistical occurrence across a population may be charted, alerting the authority to an outbreak of a disease in numbers greater than would be expected across the monitored population.

A further embodiment of the invention allows correlation of the billable work (Current Procedural Terminology code or CPT code) involved in the medical imaging procedure with the clinical presentation (provider's reasons for having ordered the examination) of the patient and eventual ICD-10 code. Reimbursement for medical image examinations from Medicare and third party payers is dependant on appropriate correlation of the examination with the patient's clinical presentation. The reimbursement level may also differ depending on the diagnosis that caused the clinical problems. In this embodiment of the invention, embedded code allows correlation of the CPT code with the ICD-10 to effect rapid and accurate billing. Optionally, the embedded coding may interact with a database to inform the radiologist of precedent threshold questions being raised by the payer. In use of such an embodiment, the radiologist's suggested follow-up regimen may be tailored to reflect the payer's requirements.

A further embodiment allows for selection of one of multiple report formats. One format for selection includes the report text alone. Another selectable format includes text and the report drawing. Another format includes the report text and selected digitized images from the medical imaging examination. Another report format includes the report text, the report drawing, and selected digitized images from the selected medial imaging examination. The several formats suggested are set forth as non-limiting examples. Formats may be configured according to needs perceived by the radiologist and may vary from one report to another.

BRIEF DESCRIPTION OF THE DRAWINGS

Preferred and alternative embodiments of the invention are described in detail below with reference to the following drawings.

DETAILED DESCRIPTION OF THE PREFERRED EMBODIMENT

Figure 1:
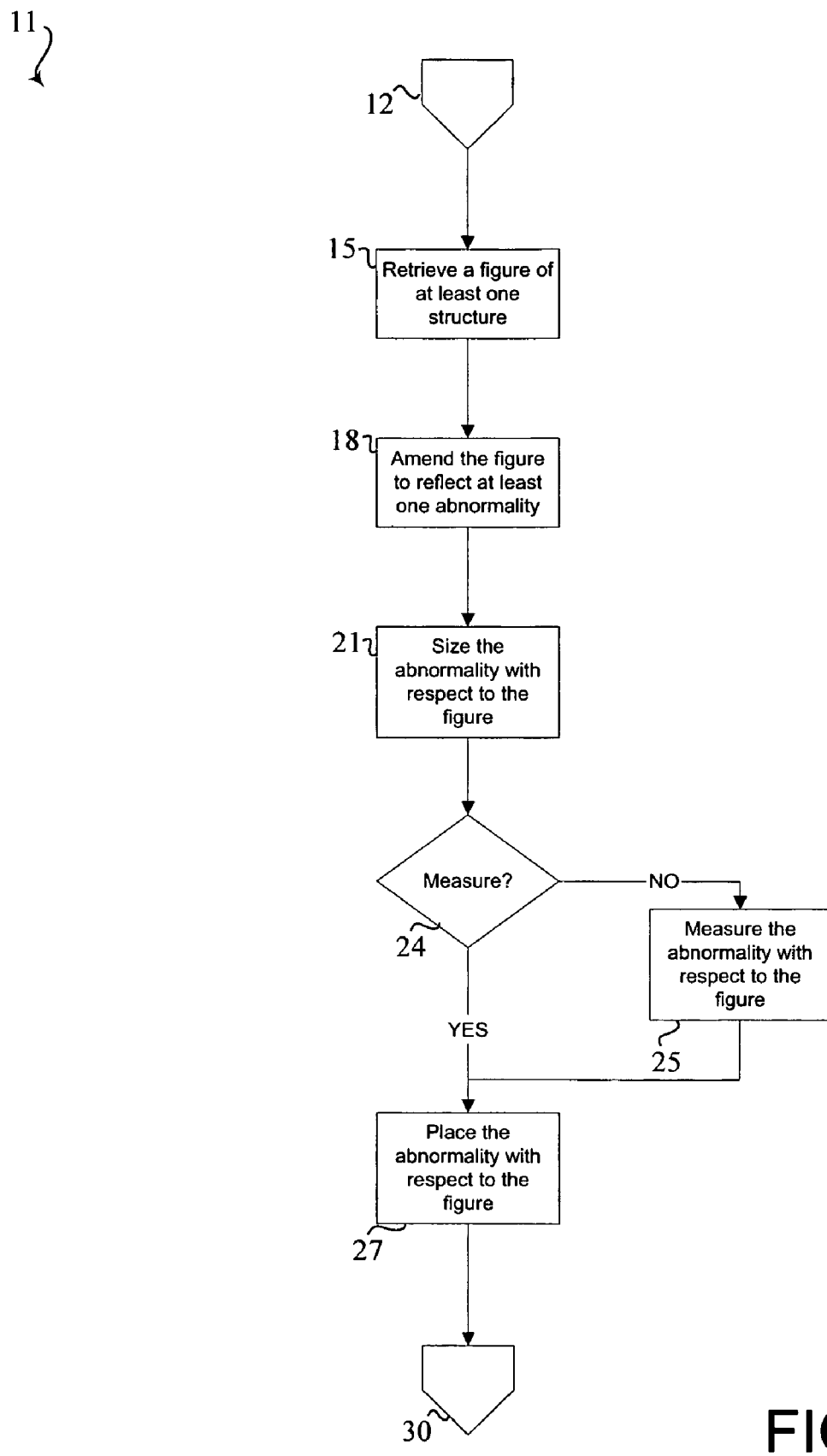
FIG. 1 is a flowchart of a method for generating a report of findings.

A method for generating a report of at least one abnormality evident on a medical image. The medical image includes at least a portion of at least one structure of the human body. The method includes retrieving a drawing of at least one structure. The retrieved drawing is amended to reflect the abnormality. The abnormality is sized and placed at a location on the retrieved drawing of the at least one structure, corresponding to the abnormalities location on the medical image. Placement of the sized abnormality generates an amended drawing representative of the medical image for inclusion in the report.

Within the teaching of this patent, the term "medical image" shall refer to any primary source of a healthcare practitioner's impressions. Under such a definition, both actual images from medical imaging devices (such as radiology films) or an examination of the actual patient the physician sees for physical exam are included. Thus, a general physician conducting a physical examination of a patient will in this parlance be included in the term "radiologist examining a medical image."

Similarly, while the "medical image" can include the observation of a live and present patient, so too, throughout this patent, the term "radiologist" refers to any examining healthcare provider using the invention to express impressions garnered from the medical image as described in the preceding paragraph. As expressed herein, the term "radiologist" might include an ophthalmologist using the invention to describe observations of the retina, or a physician's assistant using the invention to describe the location of a contusion. In the terms of this patent's teaching, the persons using the invention will all be referred to as "radiologists."

Within the teaching of this patent, an embodiment of the invention allows radiologists to formulate radiology reports and to communicate a medical image interpretation by selecting drawings that represent abnormalities accompanied by designatable descriptive text. The drawings that the invention either retrieves or generates, as a representation of a medical image, will be called "drawings." The invention works by retrieving drawings to represent a perceived condition, disease, or anomaly in an organ, structure, location, or space within a portion of the body under examination, collectively referred to herein as an "abnormality." Upon designating the anatomic structures of an examination, the invention will retrieve a idealized specific drawing which will include only the portions of a body that are under examination. The retrieved drawing will be an idealized normal representation of the anatomy included in the given imaging exam.

Once the generic idealized normal representation or "idealized drawing" is retrieved and presented to the radiologist, the radiologist, through judicious selection of representative abnormalities, directs the invention to suitably generate an altered drawing to show an abnormality located on the otherwise normal or idealized generic drawing. The resulting drawing is referred to as an "once-altered drawing." A "twice-altered drawing" is similarly a drawing altered to show both a first and a second abnormality, each suitably located on the otherwise normal or idealized generic drawing. In the same fashion, the drawings are named until a "final altered drawing" shows the several abnormalities, each suitably located on the otherwise normal or idealized generic drawing.

Three verbs are also necessary to describe the interaction of the invention with the radiologist. In an interaction between the radiologist and the invention, where the radiologist indicates by activation of a software means to select from a number of alternative states may be alternately described as "Clicking" or "to click" meaning, in at least one embodiment, to press and immediately release the mouse button. To "click on" something is to position the indicator or pointer directly over that something and then click or activate a software response. Additionally, "clicking" refers to, as well, any other software means to input information into a system by means of selecting from a plurality of choices including by voice recognition means, keyboard manipulation, or touch screen activation. Where software means exist to use eye movement, neural activation, other not yet fully commercialized means to select from a plurality of choices, these means, too, are included in the verb "to click."

"Retrieving" is the act of retrieving a stored idealized drawing of either structures or organs or of abnormalities in response to radiologist's clicking along with such data as is associated with the idealized drawing to make up a data association. Where an idealized drawing is altered to include an abnormality suitably located on the idealized drawing that the radiologist has observed on the medical image an image is generated. To "generate" refers to the alteration of an idealized drawing representing normal findings. "Generate" also refers to retrieving a stored image but adds the further step of developing a composite of retrieved drawings according to radiologists selections or clicking. Images representative of normal anatomy are "retrieved" rather than "generated."

An embodiment of the invention is described in a flowchart. Referring to FIG. 1, a method for generating a radiological report 11 continues after the radiologist is presented with a medical image for analysis at an off-page block 12. At a block 15, a radiologist is presented with a idealized drawing retrieved to represent the content of the medical image. The selection may be according to several alternate means. For example, an examination of a specific part of a patient was performed according to a healthcare provider's orders. A retrieved drawing representative of the structure and view specified in the order may be automatically selected. Alternatively, the radiologist might retrieve a drawing or a plurality of drawings for comparative selection by means of uttering or keyboarding a keyword, such as "kidney" or "left kidney" and "coronal view" to be more specific. Where a plurality of drawings is suitably retrieved in response to the keyword, the radiologist might select the most suitable from among them.

Another alternative is by "smart" recognition of the image. For instance, as in facial and other pattern recognition software currently available, a number of indicia may be present in the medical image. For instance, where present in a medical image, the distinctive arches of ribs offer sufficient information to allow immediate location and orientation of an image. Similarly, where either intestine is present in the medical image, the distinctive shaping of the intestine allows recognition of the anatomical features present in the medical image and, thus, a representative drawing is readily retrieved. More refined protocols would allow precise definition of the boundaries of the medical imaging, but a drawing selected for retrieval would readily be designated by the indicia present in the medical image.

The radiologist may then alter the drawing to conform it with any abnormalities the radiologist perceives on the medical image. After the radiologist retrieves a suitable idealized drawing, the radiologist then retrieves a palette of drawings of abnormalities and places one of them according to the location of the abnormality on the medical image.

Thus, where a mass is perceived in an organ or structure displayed on the medical image, the radiologist may, by, for example, clicking on an icon or initiating a keyword search, describe the mass with such terminology as the image warrants. In response to the radiologist's judicious selection of suitable icons, keywords, or other means, exemplar drawings of diseased or damaged organs or structures are responsively retrieved. Thus, if a solid mass appears in the medical image, the radiologist clicks on an exemplary mass or utters or input the words "mass" or "solid mass" that responsively invokes a palette of drawings of masses typical to such a mass in the kidney (assuming the kidney to be the structure of the radiologist has selected). If the medical image of mass exhibits characteristics that allow the radiologist to more readily identify the mass, the radiologist suitably clicks on or utters or inputs the word "lymphoma" or "metastasis" to retrieve a more particular palette of drawings suggesting possible matching abnormalities.

Again, as with the retrieval of the generic idealized drawing used to begin drafting the radiologist's report, a "smart" means may optionally be used to select a particular palette of drawings representative of perceived abnormalities in the medical image, allowing the radiologist to compare features presented in an exemplary drawing with those on the medical image. The selection of one of the presented palettes of exemplary drawings allows the radiologist to select the most appropriate match to the structure or organ observed on the medical image. Indicia that a suitable computer program perceives on the medical image trigger selection of suitable drawings of abnormalities for presentation in the palette.

Whether the "smart" means or the radiologist himself makes the selections of abnormality drawings that are used to populate the palette, the radiologist may optionally elect to make further selections from another proffered palette of drawings to suitably represent an abnormality in the medical image. Where none of the drawings on the palette of drawings is suitable, in the radiologist's view, to describe the abnormality on the medical image, the radiologist's clicking on a suitable icon retrieves a distinct palette of drawings of additional abnormalities. The radiologist and the radiologist's selections from proffered palettes will dictate what suitable alteration of the retrieved drawing is necessary to indicate the presence of the perceived abnormality.

At a block 18, the idealized drawing is altered according the radiologist's selections to reflect in the altered drawing the presence of the abnormality perceived on the medical image. In one embodiment of the invention, an altered drawing is generated by the superimposition of an exemplar drawing of the selected abnormality onto the retrieved idealized normal drawing of the structure. Alternate means will work as well, so long as the altered drawings follow a "structure plus abnormality" construct. Further refinement of the amended generated drawing allows placement and orientation of the drawing of the perceived abnormality.

At a block 21, the retrieved drawing of the perceived abnormality is sized with respect to the retrieved idealized normal drawing representing the structure or organ under study in the medical image in order to present the drawing of the abnormality in proportion to the idealized normal drawing on which the drawing of the abnormality is placed. By using such a method, a radiologist may also indicate a perceived size of a structure in the medical image to be the abnormality. For instance, atrophy of an organ might be the finding shown by a shrunken organ in the idealized normal drawing. To indicate an abnormally sized structure, the radiologist may retrieve a idealized drawing of the structure and by means of suitably activating icons on a display, size a drawing of the structure relative to the retrieved idealized normal drawing in which the sized drawing will reside. In such a fashion, the radiologist may enlarge a retrieved drawing of a heart and place the enlarged drawing within a retrieved idealized normal torso to indicate a perceived enlargement of the heart in a once-altered drawing.

In other instances, the abnormality is either a localized defect or a localized inclusion in the structure under study. In such instances, precise placement and orientation of the structure is necessary in order to suitably describe the abnormality as it exists in or on the structure. By comparison to the medical image, the abnormality is sized with respect to the structure or organ under study.

Where direct measurement of the abnormality in the image is possible and desired, at a block 24, the method includes that measurement at a block 25. The scale of the image allows direct measurement in most cases. Given the diversity of collection means available for producing medical imaging and the diversity of means for presenting the medical imaging to the radiologist, the scaling of any measurement from the imaging varies widely. It is possible for the radiologist to select and to appropriately proportion abnormalities with reference to the idealized normal drawing. In one embodiment of the invention, on screen cursors placed over the medical image allow for direct measurement and determination of orientation of major and minor axes of the abnormality and the measurements are used to generate a "first estimation" for retrieving and sizing the retrieved drawing of the abnormality according to the measurements. The radiologist makes the final adjustment of the retrieved drawing of the abnormality to achieve suitable proportionality.

At a block 27, the abnormality is placed on the figure for incorporation of the abnormality on the finished figure. Navigating the abnormality onto or into the figure might be by indicator means, such as by use of a mouse or trackball, or by voice actuated means, such as interaction with voice-actuated software. Use of tracked eye movements or simple "arrowing" on a keyboard alternatively serves to place the abnormality. Once placed, the figure is suitably harmonized to indicate the presence of the abnormality in a generated figure representative of the abnormal structure. Exemplary text is retrieved according to an activation of the software to formulate a query by movement of the indicator over either a drawing or text.

Further processing of the report in accord with the generated drawing representative of the abnormal structure occurs at an off page indicator 30. Such processing alternatively includes embedded coding of the abnormality, and text generation in accord with the altered drawing. Further examination aids might be implicated by the presence of the conditions in the generated drawing, and, thus, presented to the radiologist for confirmation or ruling out. Particular follow-up studies might be presented to the radiologist for consideration based upon the generated figure.

One embodiment of the invention is practiced in interaction with a computer. A first exemplary screen 31 of the embodiment is presented in FIG. 2. Arranged about the screen in a fashion to be analogous to a radiologist's report of abnormalities are the clinical presentation datum 33, a drawing 42 representing the ordered medical imaging, a measurement aid 60*a*, a cross-section selection aid 63, a findings paragraph 36*a*, and an impression paragraph 39*a*. Additionally, a microphone icon 66 is present to allow the radiologist to activate a microphone connected to the computer in order to dictate a specific abnormality or to amplify the generated report text.

Generally, the radiologist views a medical image (not shown) either simultaneously, in a "hard copy" such as a radiological film, as a computer generated image on a screen of a computer, or as a pane in a graphic user interface such as WINDOWS™, while viewing a pane or screen containing the display of the embodiment of the invention.

The term "medical imaging" will comprise information garnered by any of a number of existing techniques including direct observation, the use of radiation (such as x-rays, or radioisotopes) or other imaging technologies (such as ultrasound and magnetic resonance imaging) to diagnose or treat disease. For the illustrative purposes of this application, discussion of computed tomography (CT) is used merely as a non-limiting example of the use of the invention for recording analysis of medical images based upon direct observation, the use of radiation, or other imaging technologies. Because analysis of CT images includes many of the more complex features that are present in imaging methods, including imaging in three dimensions, and adjustable image grey scale window and level settings, CT has been selected as the exemplary imaging method for teaching the invention.

For the purposes of the discussion, the example of a medical image is selected to be a scanogram or other coronal image of a patient produced by means of CT. A scanogram is an image obtained by moving the patient through a CT gantry, that is, through the plane of the X-ray source and detectors, while X-ray projection measurements are made at a fixed source angular position. The medical image obtained in this manner is similar in general appearance to a conventional projection radiography image. The scanogram has lower spatial resolution but much wider dynamic range. Some form of edge enhancement filtering or dynamic range compression is often applied before display of the medical image. Scanograms are used primarily to localize body structures for subsequent CT scans, especially by graphic plane prescription, and to display the locations of acquired CT slices. A variety of equivalent names have been given to this technique including: ScoutView™, Pilot Scan™, Surview™, Topogram™, Scanoscope™, radiographic mode and localizer image.

While CT is useful in illustrating the nature of the invention, any form of medical or radiological imaging suitably serves as a basis of a radiologist's opinion, and therefore, embodiments of the invention will suitably serve the radiologist in formulating a report of opinion, regardless of the type of medical or radiological imaging that forms the basis of the radiologist's opinion.

Computed tomography (CT) is a planar, transaxial imaging method providing excellent contrast resolution, which can be used to evaluate the musculoskeletal system. Computed tomography (CT scanning) can often define alterations in soft tissue and bone that are undetectable with conventional radiography because of its cross-sectional display, excellent contrast resolution, and ability to measure specific tissue density attenuation values. CT scanning is also capable of making quantitative measurements of bone mineral content. CT images are produced in computers, which allow reformation of transaxial data in the coronal or sagittal plane and three-dimensional analysis of image data.

The use of CT numbers, or Hounsfield units (HU), provides an indication of the nature of the tissues being imaged. For example, an abnormality with an attenuation value close to that of water is likely to be a cyst. The measurement of attenuation values of intraosseous abnormalities may be somewhat difficult, however, especially in narrow bones in which the contribution of the cortex may prohibit accurate assessment. For imaging bones, a near-maximum window width (1,000-2,000 HU) and a relatively high window level (200-250 HU) allow good visualization; for soft tissues, a window width of 400-600 HU and a window level of 0-100 HU are generally acceptable.

A non-exhaustive list of HU values includes: Bone at 1000 HU; Liver tissue at 40-60 HU; White matter (brain) at 46 HU; Grey matter (brain) at 43 HU; Blood at 40 HU; Muscle at 10-40 HU; Kidney at 30 HU; Cerebrospinal fluid at 15 HU; Water at 0 HU; Fat at −50 to −100; and Air at −1000 HU. Examining CT images at various limits of grey scales values (called the window) centered on the approximate density of a particular tissue (called the level) of interest allows the radiologist to selectively examine different tissues/organs in a given exam. This flexibility and concept are utilized in most digitized imaging.

The administration of a radiopaque contrast material into blood vessels can be a useful adjunct to CT in the analysis of the blood supply in normal or abnormal tissue. The absence of blood supply may indicate an abnormal structure is a cyst, hematoma, or abscess. The detection of a blood supply by observing density change or "enhancement" after injection of intravenous radiopaque contrast in an abnormal structure may indicate that an abnormality is a tumor.

As indicated above, a scanogram can suitably be used to display the locations of acquired CT slices. As such, the scanogram is as an analogue to an index of the vast information collected while performing a CT scan. In fact, the scanogram is a compilation of the many acquired CT slices available for viewing or analysis. By virtue of the spatial location of each data point within the CT slices, three-dimensional displays of the scanned tissues can be generated. Three-dimensional display of CT information helps in the imaging of regions of complex anatomy. Such displays facilitate surgical planning and even allow rehearsal surgery of complex reconstructive procedures.

CT can be used to evaluate many regions of the body including the intracranial, thoracic, abdominal, and pelvic anatomy as well as a variety of musculoskeletal disorders. CT scanning allows detailed analysis of structures that were previously only visible by surgical dissection. CT scanning is of value to assess trauma (fractures, organ and vascular injuries), infection (osteomyelitis, abscesses), hemorrhage, hematomas, neoplasms, obstructed tubular structures such as the biliary tree, Urinary tract, and bronchial tree), renal stones, joint disease, vascular lesions (aneurysms, arterial entrapment syndromes, atherosclerosis), congenital or metabolic disease, and low back pain. In the spine, CT has largely replaced conventional x-ray tomography as the technique of choice after routine radiography in the evaluation of complex fractures and dislocations both for diagnosis and planning complex surgical reconstruction. In musculoskeletal neoplasms, CT has not replaced conventional radiographic techniques, but combined with MR it has become more important in the surgical planning for treatment of primary bone neoplasms.

Figure 2:
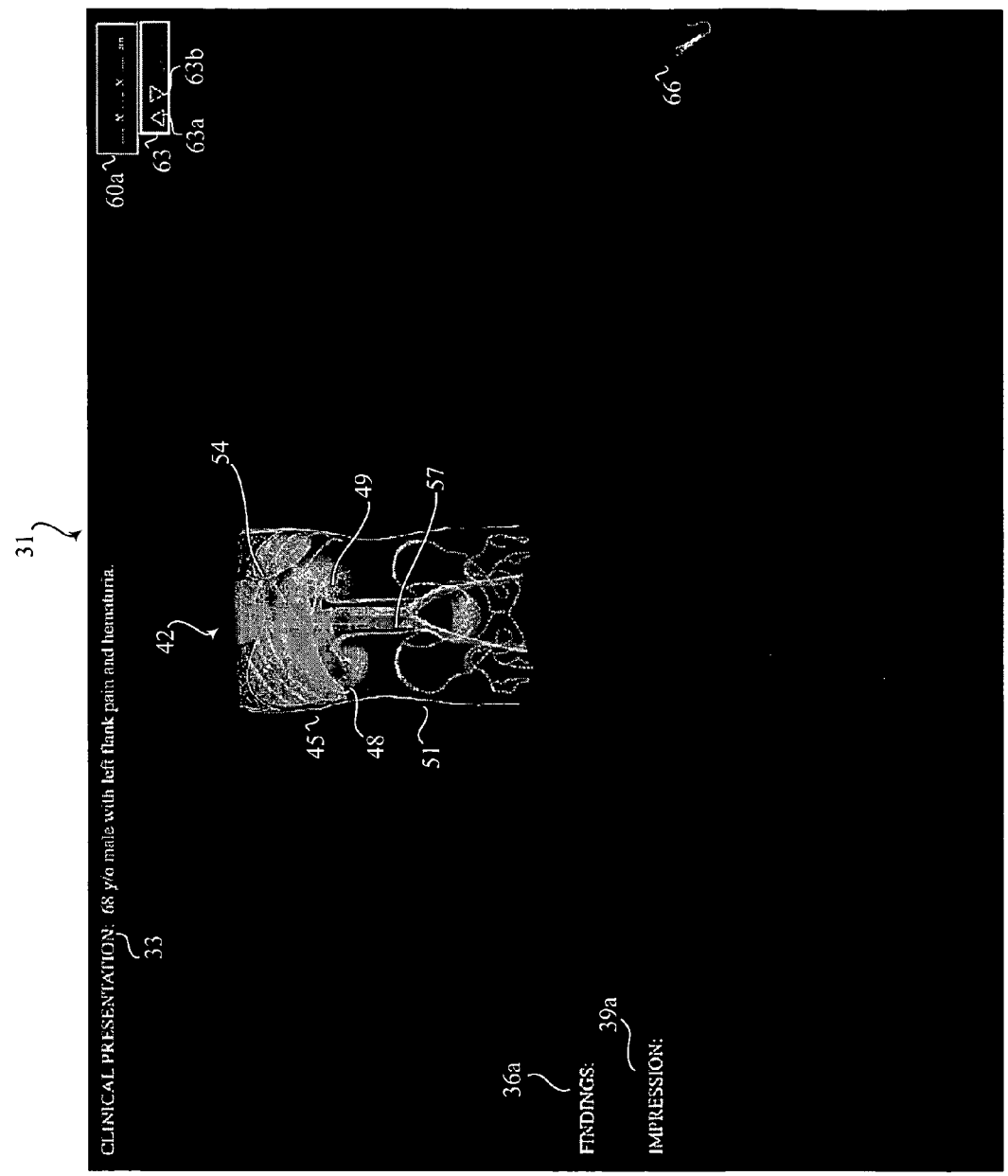
FIG. 2 is a first exemplary screen of showing formation of a report of radiological findings.

In FIG. 2, an idealized radiologist's desktop 31 is set up to include important features the radiologist's report will comprise. Included on the radiologist's desktop is the drawing 42 the radiologist has retrieved, in this case, a coronal or frontal view to include anatomic features as the radiologist has deemed relevant as a generic idealized normal representation of a medical image. Structures such as the rib structure 45, the spleen 54, the right kidney 48, the left kidney 49, the pelvis 51 and the spine 57 are illustrated. Alternatively, the drawing 42 was automatically retrieved according to the orders of the healthcare provider who ordered the medical images to be taken. If the radiologist did not specifically retrieve the drawing 42, or if the drawing 42 does not show what the radiologist desires, the radiologist may either retrieve other drawings 42 that, in the radiologist's opinion, more closely represent the medical image, or may, by direction, move the boundaries of the drawing to include or exclude relevant organs. As presented in the FIG. 2, the drawing 42 represents the anatomic structures that the radiologist wants to report on.

Additionally, the radiologist's desktop 31 includes the clinical presentation that the primary healthcare provider's included to order the medical examination imaging. Additionally, the radiologist's desktop provides a findings heading 36a and an impression heading 39a that are generally included in a traditional radiologist's report. Additionally, the radiologist's desktop includes a microphone icon 66 for initiating either an external voice recognition software such as Dragon Naturally Speaking™ or an internal voice recognition engine. While not a necessary feature of the invention, it is an intended option that navigation and inputting may be done by recognition of voice commands.

The radiologist's desktop further includes an additional aid to the radiologist, an adjusting block 63 used with a dimensional aid 60a. The radiologist uses the dimension block 60a as one of several alternate means by which to establish dimensions for abnormalities to be placed in the drawing 42 that are perceived in the medical image. The ability to shrink and to grow a drawing of an abnormality within the drawing allows the radiologist to adjust the size of the abnormality relative to the drawing in order to achieve a more representative drawing than would be possible strictly by deriving a size of the abnormality based upon a simple measurement of the abnormality on the medical image. Because bodies vary in size, it is advantageous for the radiologist to be able to adjust by use of the adjusting block 63 in order to achieve that proportionality. Because the drawing is inadequate for conveying absolute dimensions of the abnormality, the dimension block 60a carries that information into the report and holds it for later insertion into a retrieved template reporting the findings.

Figure 3:
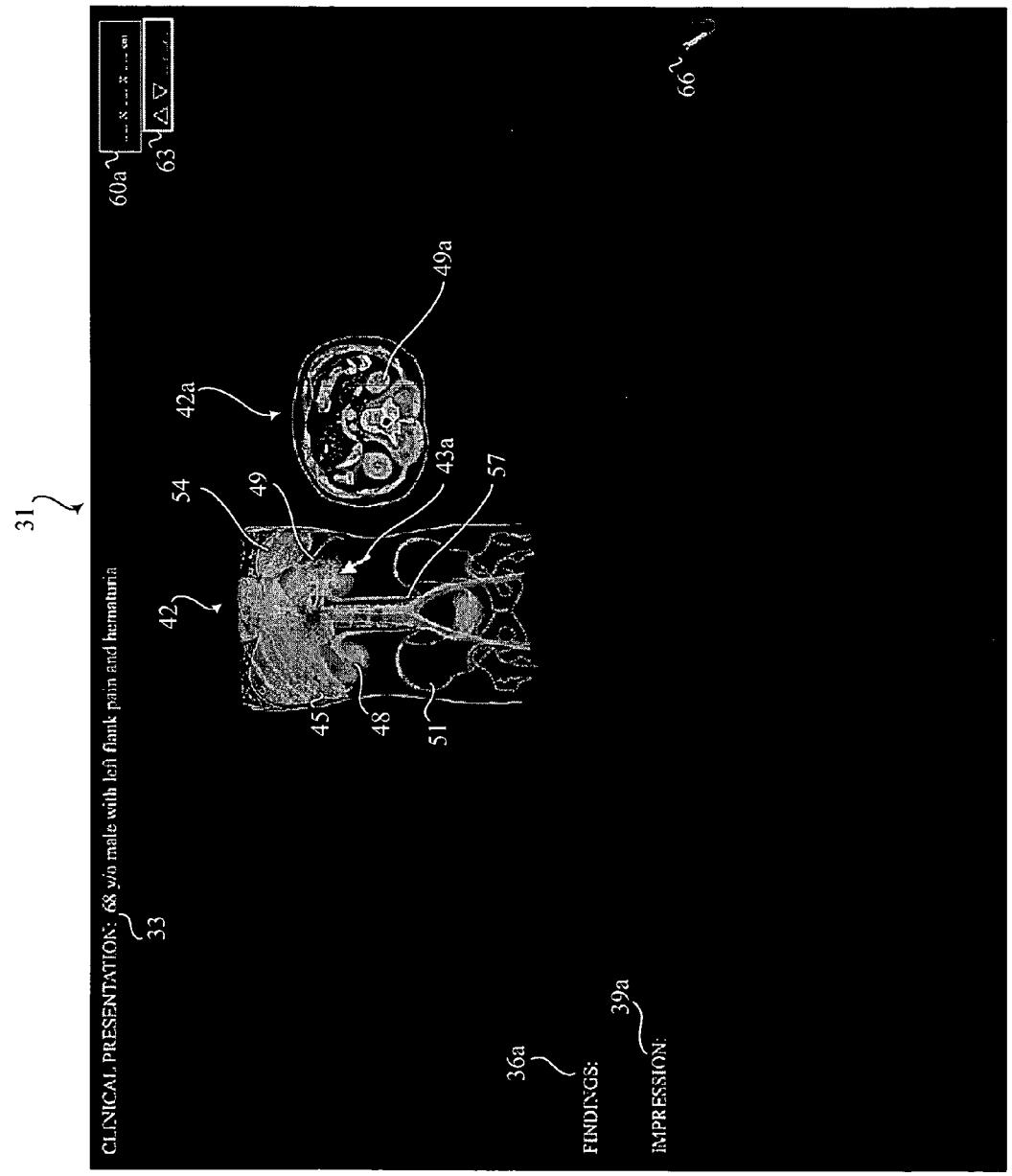
FIG. 3 is a second exemplary screen of showing formation of a report of radiological findings.

FIG. 3 shows the radiologist's desktop 31 after the radiologist has indicated a locus on the drawing from which a cross-sectional drawing 42a of the torso, consistent with a slice of the torso at the selected locus, is drawn. The cross-sectional drawing 42a allows the radiologist to place additional information into the report as to a location of the abnormality perceived on the medical image. To indicate the locus of the desired cross-sectional drawing, the radiologist has maneuvered an indicator 43a to indicate a cross-section at a level of the left kidney 49. The embodiment retrieves the cross-sectional drawing 42a in response to the radiologist clicking at the locus of the indicator 43a. Alternatively, to assist in selection of a suitable cross-section drawing, the adjusting block 63 may also advantageously be used to indicate the radiologist's desire to take either a higher or lower cross-section 42a on the torso, according to selections of either of the up icon 63a or the down icon 63b. Once a suitable cross-sectional drawing 42a is selected, clicking on the cross-sectional drawing 42a returns the adjusting block 63 to its use to dimension abnormality drawings relative to the drawing 42 or the cross-section drawing 42a.

Figure 4:
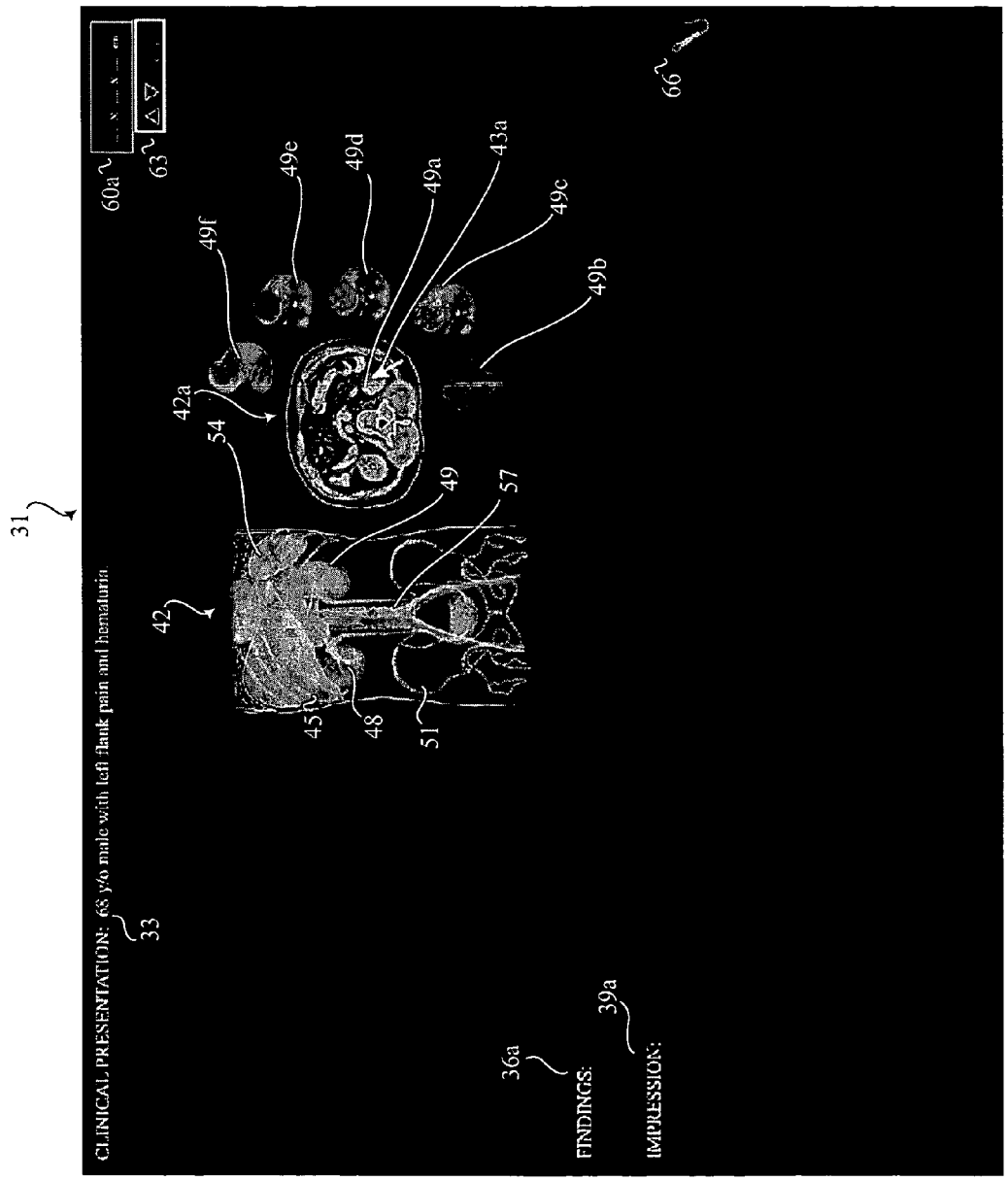
FIG. 4 is a third exemplary screen of showing formation of a report of radiological findings.

Referring to FIG. 4, included in the cross-sectional drawing 42a is a cross-section 49a of the left kidney 49. The cross-section 49a of the kidney is especially useful in placing an abnormality within the drawing 42. By moving the indicator 43a, and clicking on the location of the finding on this axial or cross-section 49a of the left kidney 49, the radiologist has instructed an embodiment of the invention to recall a number of abnormalities commonly found in the structure or anatomic location associated with the location where the indicator 43a rests. In this case, the location of the indicator 43a causes the embodiment to retrieve kidney cross-section exemplary drawings 49b, 49c, 49d, 49e, and 49f, representing abnormalities commonly involving the kidney.

Figure 5:
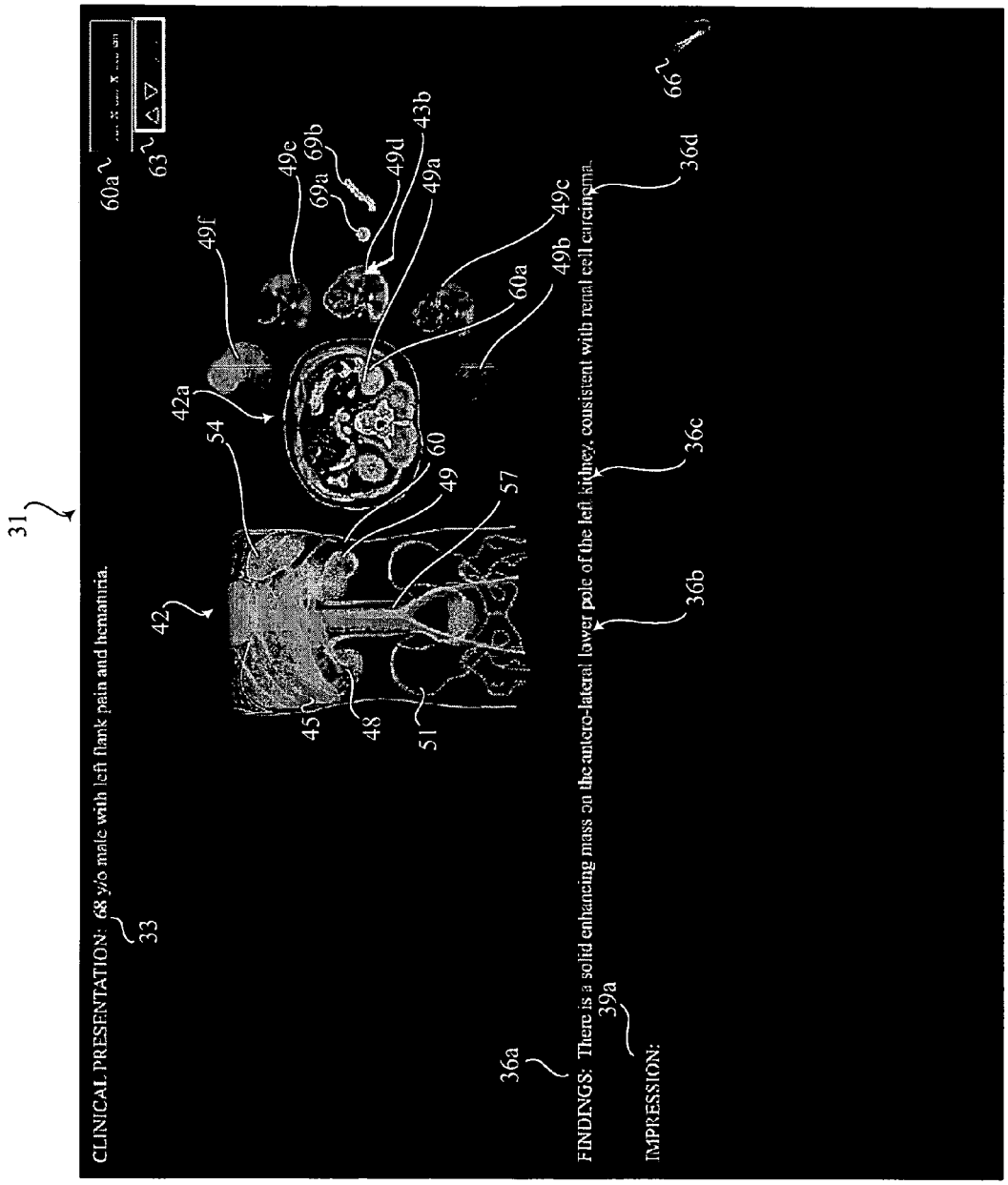
FIG. 5 is a fourth exemplary screen of showing formation of a report of radiological findings.

Referring to FIG. 5, the radiologist's desktop 31 retains the features of FIG. 4. Clicking on one of the several retrieved kidney cross-section exemplary drawings 49b, 49c, 49d, 49e, and 49f, showing representative abnormalities associated with common conditions of the kidney, has evoked the embodiment to supply a textual finding 36b under the Findings heading 36a that are configured to suitably describe the abnormality's characteristics, what it represents, and its location, which the embodiment appended onto the findings paragraph 36a. The textual findings 36b under the "Findings" heading 36a include the implicated organ 36c, the one recalled according to the indicator 43a, and the likely diagnosis of the selected abnormality 36d, and, had they been placed, the dimensions from the dimension block 60a. Where multiple organs are implicated, each selection of an organ and a condition appends further textual findings 36b onto the findings paragraph 36a.

The textual findings 36d that the inventive tool supplies in response to selections by the radiologist may be designated by a healthcare professional and stored in association with the drawing of the abnormality at the time of programming or, alternatively, by a chief radiologist or some other representative of the hospital or clinic hosting the service upon installation at the hospital or clinic or at selected times thereafter in order to supply a textual standard for reporting a particular abnormality. Additionally, International Classification of Diseases (ICD-10) coding may be associated with the selected drawing of the abnormality. The National Center for Health Statistics (NCHS), the Federal agency responsible for use of the International Statistical Classification of Diseases and Related Health Problems, 10th revision (ICD-10) in the United States, has developed a clinical modification of the classification for morbidity purposes. The ICD-10 is used to code and classify mortality data from death certificates as of Jan. 1, 1999.

In a preferred embodiment of the invention, a developer's desktop (not shown) is implemented to conform exemplary textual findings and suitable ICD-10 coding and to suitably associate the exemplary textual findings with the supplied abnormality drawings to enable retrieval of the exemplary textual findings and ICD-10 coding upon selection of a supplied abnormality drawing. Additionally, the developer's desktop will allow modification and addition to the set of supplied abnormality drawings as medical needs require. If, due to epidemiological reasons, what had been a highly improbable diagnosis in a region becomes more likely, a new drawing indicating the pathology of the diagnosis is stored in the embodiment and suitable textual findings and ICD-10 coding are associated with the drawing. At the chief radiologist's desktop, the drawing is further associated with a locus to allow its retrieval in response to the radiologist's activation of the indicator 43a or clicking as described above with reference to FIG. 4. Thus, the radiologist clicks on a kidney, among the exemplary abnormality drawings 49a-f presented in response to activation will include kidney cross-section exemplary drawing 49d, which will also result in the embodiment retrieving and supplying suitable textual findings 36, that include the keywords "antero-lateral lower pole" 36b and "left kidney" 36c, indicative of location, and diagnosis "renal cell" carcinoma 36d indicative of the nature of the abnormality noted in the medical image.

Where the radiologist has placed dimensions in the dimension box 60a, the retrieved and supplied exemplary textual findings 36 will also include dimensions 60b of the abnormality that are associated with the selection of kidney cross-section exemplar 49d and the renal cell carcinoma exemplary textual findings 36d. The retrieved and supplied textual findings serve as a template for the embodiment to fill with the dimension 60b and to append to the "Findings" heading 36a.

In one presently preferred embodiment, the application is run on a two-screen computer system (not pictured). In such an embodiment, medical image compiled according to a digital imaging and communications in medicine (DICOM) protocol is stored in large archives as are used routinely, though the invention is not limited only to DICOM images. In the embodiment, the inventive software and system will retrieve medical images according to requests inputted by the radiologist for display on a second display screen while the radiologist composes the radiologist's report on the radiologist's desktop 31 on the first display screen by interaction with an embodiment of the invention. Thus, especially where dimensions are involved, the embodiment further assists the radiologist by allowing, for example, information as to the location of a displayed portion of a CT cross-section medical image to make an initial selection of a cross-section drawing 42a to use as a idealized normal drawing 42. Measuring an abnormality on the medical image will supply dimensions to the dimension block 60a. An interface with a medical imagery database, according to a suitable protocol such as DICOM™, is included in an embodiment of the invention.

Finally, where the medical image exists as a series of data in a database, the radiologist may select a display of the data as indicated above and may append the displayed data subset of the medical image as an illustration in the report either in addition to or in lieu of the drawing 42. The radiologist may select portions of the medical image to append to the text of the report in order to amplify the text of the report.

In an additional embodiment of the invention exploiting such a protocol, once a medical image has been recalled from a database such as DICOM™, the embodiment will allow navigation through the medical images by using the embodiment. As indicated above, the embodiment has an interface with the DICOM™ software allowing the radiologist's movement through the drawing 42 to retrieve and display corresponding medical images in response to the radiologist's requested movement. For instance, where medical images include a liver, the embodiment of the invention would summon a display of the medical images assigning a grey scale window and level setting optimal for examining tissues stored in the image in HUs from 60 HU to −100 HU.

Because the kidney is the organ under study, the embodiment formulates a request according to the DICOM™ to enhance the contrast and discrimination between tissues of interest in the medical image such that the liver tissue at 40 60 HU; Blood at 40 HU; Kidney at 30 HU; Cerebrospinal fluid at 15 HU; Water at 0 HU; Fat at −50 to −100 are optimally visualized on the display, thereby allowing the radiologist to view the kidney with enhanced discrimination of salient features of the liver and kidneys.

Conversely, should the radiologist assign such values to the display of the medical image, the embodiment, in turn, will only recall such exemplars as would relate to abnormalities susceptible to detection according to such display constraints. By integrating the medical image display software with the inventive software or system, the embodiment can make more predictive selections of exemplars according to the display parameters asserted by the requesting radiologist, thus making the radiologist more productive at the primary task of interpreting the medical images.

Figure 6:
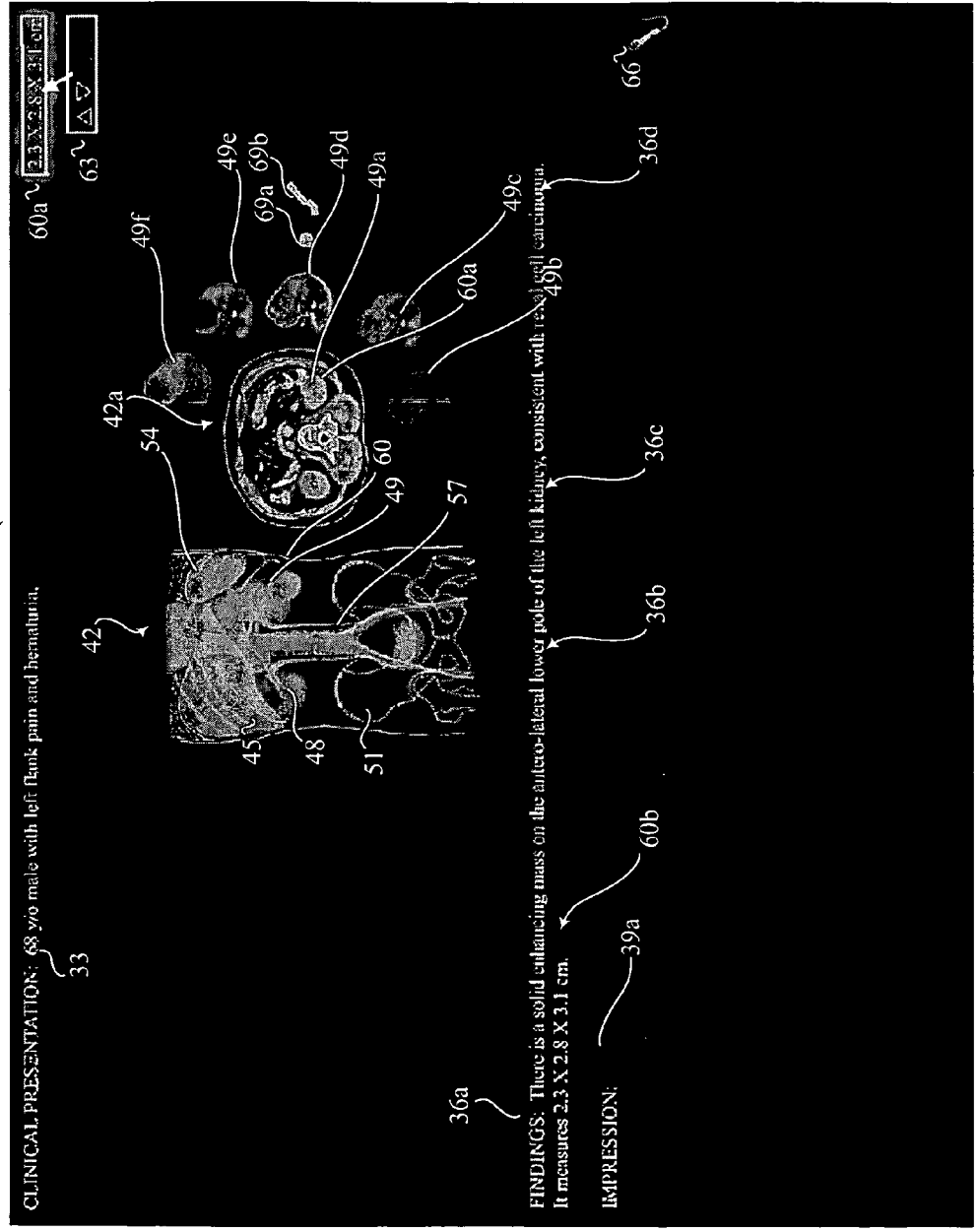
FIG. 6 is a fifth exemplary screen of showing formation of a report of radiological findings.

Referring to FIG. 6, the radiologist's desktop, in one embodiment, also includes the microphone icon 66 that allows customizable input into the textual findings paragraph 36a. In one embodiment, activation of the microphone icon 66 by clicking will initiate a speech recognition engine for receiving a radiologist's dictated findings or impressions, thus allowing the radiologist to customize the textual findings 36a and include text to reflect such variations as the radiologist perceives in the medical image. The radiologist will also have the option to click and add or delete text with a keyboard The radiologist clicks on the microphone icon 66, toggling the speech recognition engine on or off. When in the off position, the speech recognition capability can be used for navigation through the medical images, for sending commands to the inventive software or system, or for requesting distinct saved textual exemplars from the exemplars evoked in response to selections of graphic exemplars such as the kidney cross-section 49b, 49c, 49d, and 49e. Thus when the microphone icon 66 is toggled in an "off" position, the radiologist might say "Show renal cell carcinoma," to show all suitable graphic exemplars. Where the inventive system or software is also used to navigate the medical images, the same command might simultaneously adjust the display of the medical images to assign the full spectrum of displayed window and level gray scale parameters to optimize visualization of structures with HUs between 60 to −100 HU thereby optimizing the display for examining renal cell carcinoma. Similar flexibility would be possible for adjusting value, contrast and hue for medical images in color.

When the microphone icon 66 is toggled in the "on" position, the radiologist may dictate the words and phrases that the radiologist wishes to augment or to edit the text in the textual findings 36a to provide a text distinct from that generated by retrieval of exemplary textual findings supplied by the software or system in response to clicking on exemplary abnormality drawings such as the kidney cross-sections 49b, 49c, 49d, and 49e. Thus, where the exemplary textual findings retrieved fail to match the medical image findings, the radiologist may compose a textual finding using conventional dictating means.

Figure 7:
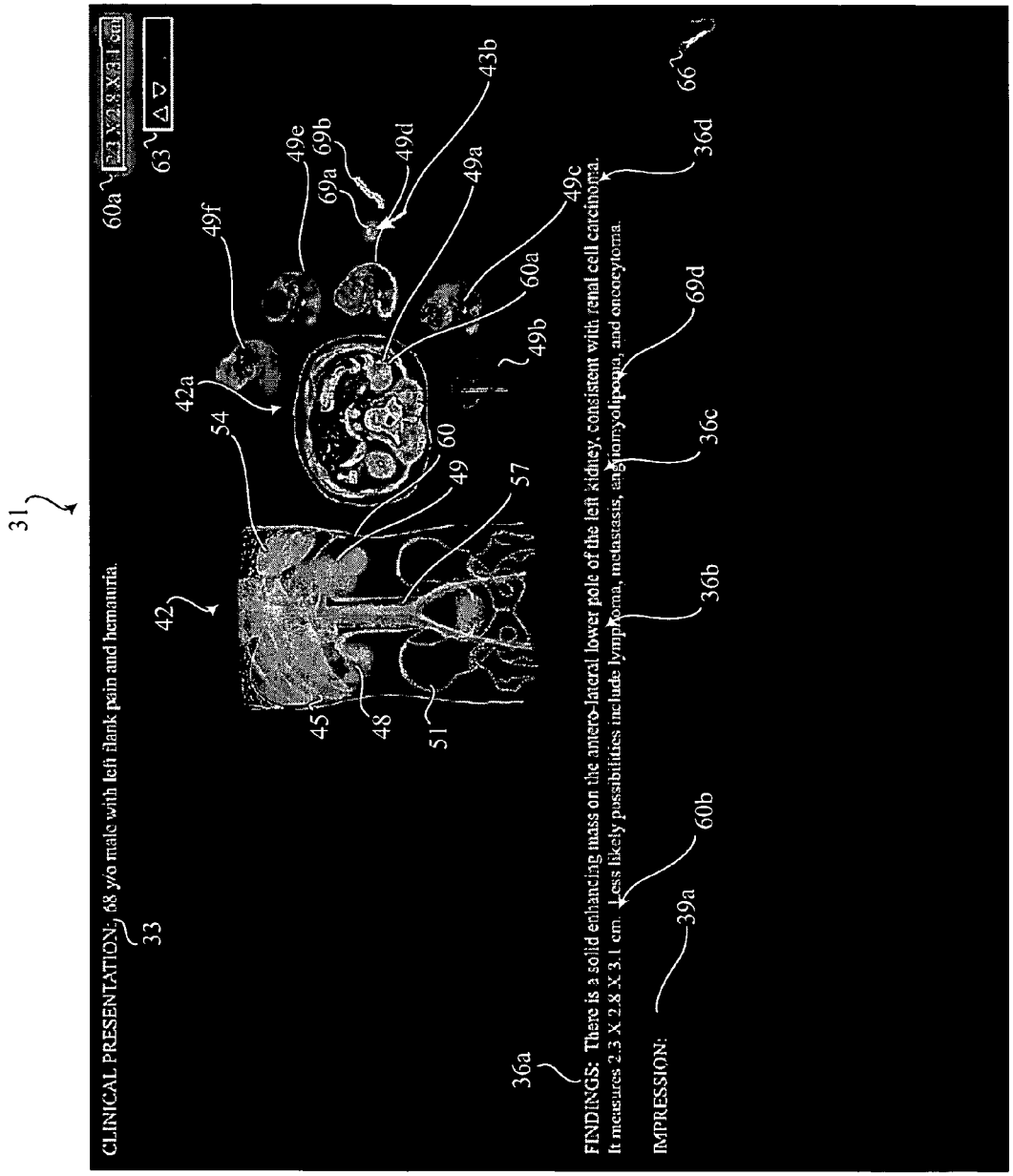
FIG. 7 is a sixth exemplary screen of showing formation of a report of radiological findings.

Referring to FIG. 7, where the evoked textual findings 36a include the correct finding (i.e. the retrieved textual findings clicking on the selected kidney cross sections 49b, 49c, 49d, and 49e match the condition the radiologist perceives in the medical image), the radiologist may elaborate on that finding by clicking on a pearl icon 69a thereby getting further amplification 69e as to the nature of the abnormality indicated. In addition, where the findings do not match, the radiologist may click on the string of pearls icon 69b. One embodiment of the invention will generate a list of abnormalities commonly associated with the disease entity detected to assist and teach the radiologist. The radiologist may then examine the medical image and determine whether other associated findings are present. A further embodiment also generates exemplary drawings of the listed abnormalities that are known to sometimes be associated with the primary abnormality. Given the additional exemplary drawings, the radiologist may choose to alter the drawing 42 to include such of the abnormalities that the embodiment associates with the additional exemplary drawings by clicking on the suitable exemplary drawing.

For abnormalities that involve an entire organ or structure, the radiologist may similarly right click on the organ or structure involved which retrieves common abnormalities that may involve an entire organ. Reporting entire organ or structure findings then follows the same process, and exploits the same use of the pearl icons 69a, strings of pearls icons 69b, and diagrams of associated abnormalities or pertinent negative findings. In addition to the completion of textual findings 36a, the string of pearls 69b works to amplify the textual findings 36a with such other associated abnormalities as generally accompany a noted abnormality. In crafting the textual findings, the radiologist may retrieve the associated finding by either selecting the representative kidney (or such selected anatomic structure) cross-sections 49b, 49c, 49d, 49e, and 49f or, instead, by clicking on such keywords as "left kidney" 36c or "renal cell carcinoma" 36d in order to retrieve suitable text selections corresponding with the keyword.

Referring FIGS. 8-11, the radiologist's desktop includes the drawing 42 appropriately altered based upon the radiologist's selections of exemplary drawings such as the kidney cross-section exemplary drawings 49b, 49c, 49d, 49e, and 49f. The drawing 42 includes other anatomic features such as the rib structure 45, the spleen 54, the right kidney 48, the left kidney 49, the pelvis 51 and the spine 57 and each is enabled for textual selection in a manner similar to that described above with respect to the kidneys. By selecting or clicking on the organ in question and selecting from the evoked exemplary drawing, the radiologist may formulate a similar report of the observable medical condition of those organs.

Figure 8:
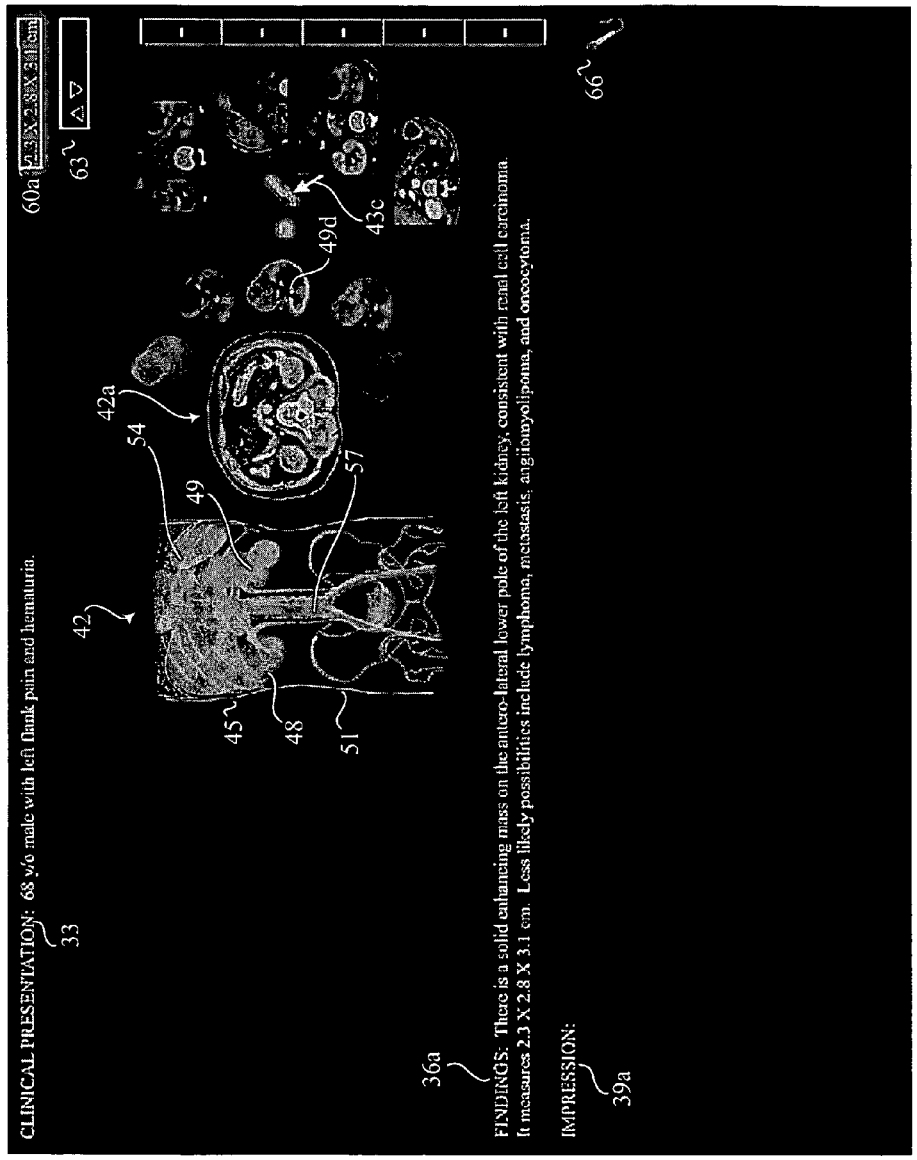
FIG. 8 is a seventh exemplary screen of showing formation of a report of radiological findings.
Figure 9:
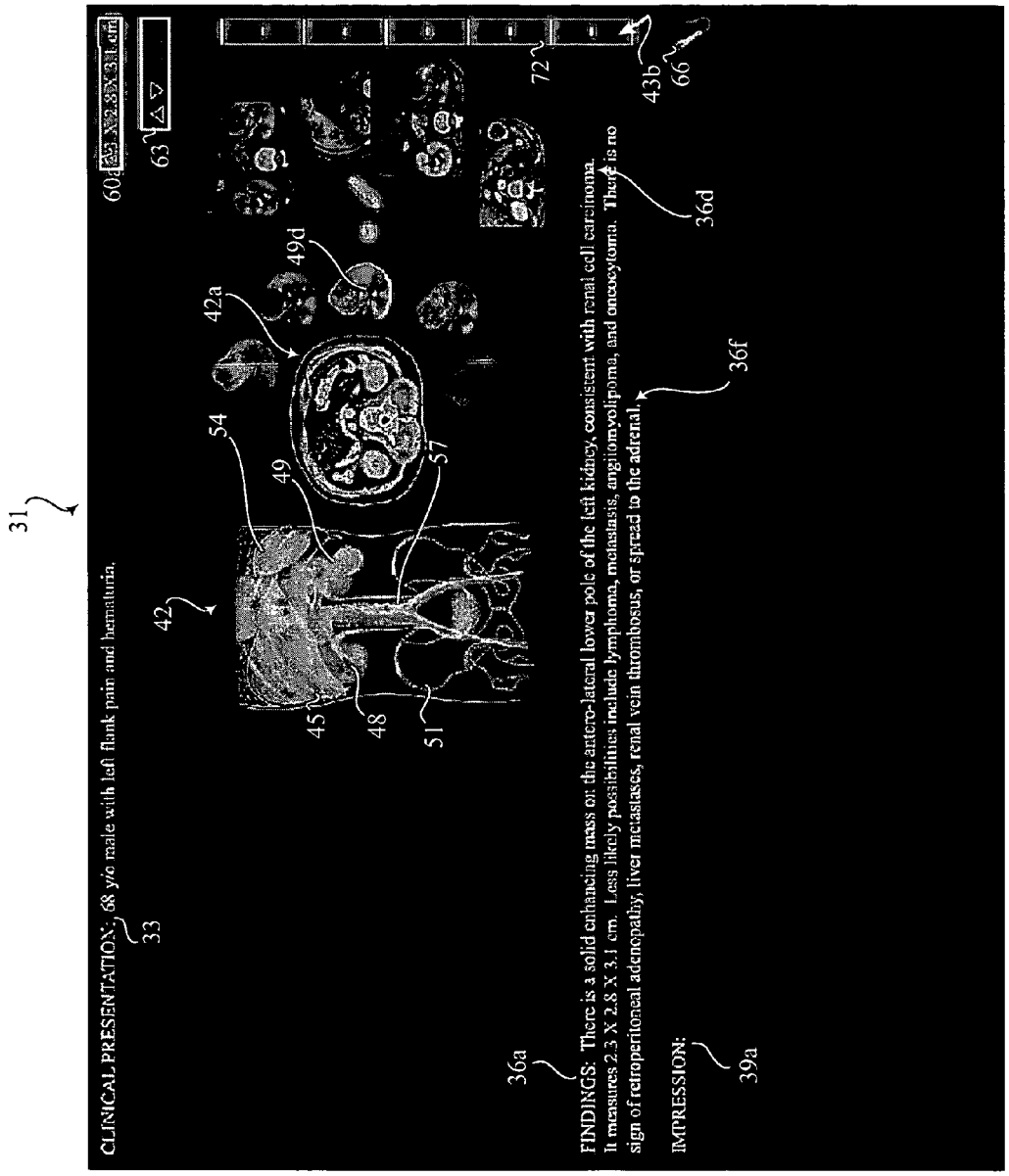
FIG. 9 is a eighth exemplary screen of showing formation of a report of radiological findings.

In FIG. 8, the generated textual findings 36a include the textual exemplar that is retrieved and supplied in accord with the selection of the desired the kidney cross section exemplary drawing 49d (along with the non-selected cross-section exemplary drawings 49b, 49c, 49e, and 49f), the cross-section view 42a including the cross-section of the lower pole of the left kidney 60a, the microphone icon 66, the pearl icon 69a and the string of pearls icon 69b, as well as appended information on the findings 36a, 36b 60b, and 69c. In one embodiment, the radiologist's desktop selectively displays the organs or structures not mentioned in the findings more faintly in the altered drawing 42 by means of a "grayed" display while the currently selected organ or structure is displayed brightly giving visual cues to the radiologist in organizing the radiologist's report.

Two means exist to assure an exhaustive report of a medical imaging examination. First, the radiologist clicks on an anatomic organ or structure in the medical drawing; then, the radiologist move the indicator 43b to click on one of the several negative finding icons 72 to retrieve text associated with the selected anatomic structure and the absence of an abnormality, thereby indicating that the anatomic structure is normal. Selecting a total organ findings diagram highlights that diagram and generates descriptive text, with the keywords describing the abnormality's identity and anatomic location highlighted. Clicking on a negative icon 72 will append a suitable negative textual finding 36*f* to the textual findings 36*a*. In an embodiment, the icons are elongated so, like a spacebar on a typewriter, the icon is readily activated with a minimum of searching.

Where such keywords as "left kidney" 36*c* or "renal cell carcinoma" 36*d* is selected and some abnormality is already included in the findings 36*a*, the selection of a negative finding icon 72, will retrieve negative findings relating to all remaining aspects of the organ or structure implicated by the keyword. For instance, where a radiologist clicks the keyword "renal cell carcinoma" 36*d* (FIG. 9) and moves the indicator 43*b* to the negative finding icon 72 to retrieves text indicating "there is no sign of retroperitoneal adenopathy, adrenal, lung or liver metastastases, renal vein thrombosis, or direct spread to adjacent structures."

Figure 11:
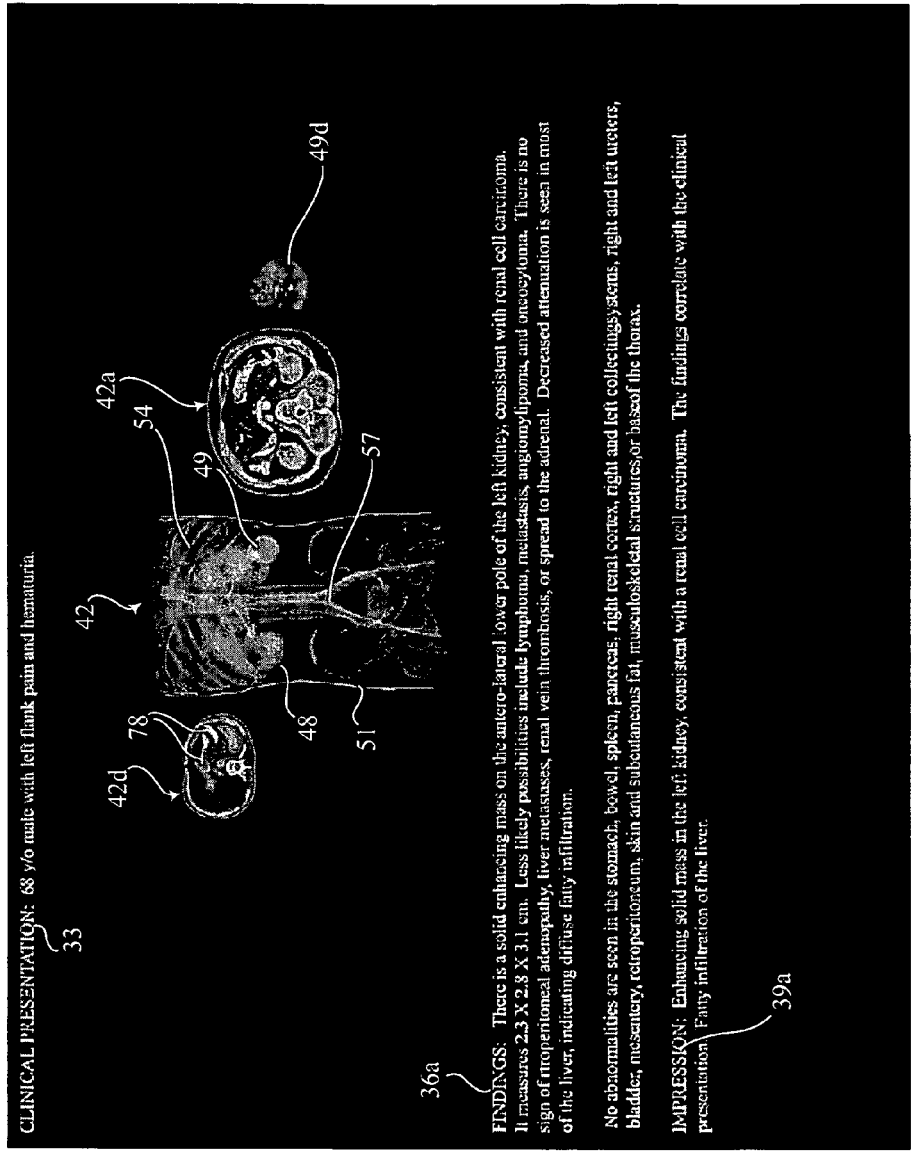
FIG. 11 is a tenth exemplary screen of showing formation of a report of radiological findings.

Referring to FIG. 11, the second way a radiologist can indicate negative medical findings occurs after the radiologist has completed the description of all of the abnormalities the radiologist has noted in the medical image. After the radiologist has completed the construct of the descriptive text and has suitably altered the FIG. 42, an embodiment finalizes the report by removing the highlighting from the keywords, removing all but the relevant graphic and text exemplars, and leaving the final (coronal and cross-sectional) anatomic diagrams. An embodiment then appends to the textual findings 36*a* an itemized list of all remaining structures remain drawing 42 that are normal. The embodiment also provides the radiologist with a final checklist before completing the report, the final checklist being configured according to the selections by the radiologist in formulating the report and according to the organs imaged in the medical image.

At any time while preparing the report, the radiologist may click on the highlighted keywords such as "left kidney" 36*c* or "renal cell carcinoma" 36*d* to include them in the final impression 39*a*, thereby including relevant textual impressions 39*a*. Just as the textual findings 39*a* are generated by selection of exemplary drawings, the impressions are generated by the supplying of exemplary textual impressions retrieved from the database as associated with the selections of the exemplary drawings. For instance, the exemplary textual impressions 39*b* are retrieved according to the content of the textual findings 36*a* as textual exemplars that have been appended by the actions of the radiologist in interaction with the system or software.

In cases in which the findings are relevant to the clinical presentation, the radiologist may note this by clicking on selected text set forth in the Clinical Presentation 33 and then clicking the Clinical Presentation heading 33 to generate a textual indication. Often little more is needed here than to confirm or to indicate that the abnormality is not related to the reason that the patient presented himself to the physician who ordered the medical imaging procedure. Where the radiologist has not specifically indicated a relationship between the clinical presentation and the abnormalities presented, the Chief Radiologist may configure the default setting. This information is very useful in the utilization review, i.e. to decide if a particular complaint is well-diagnosed with the type of medical imaging that was ordered.

Figure 10:
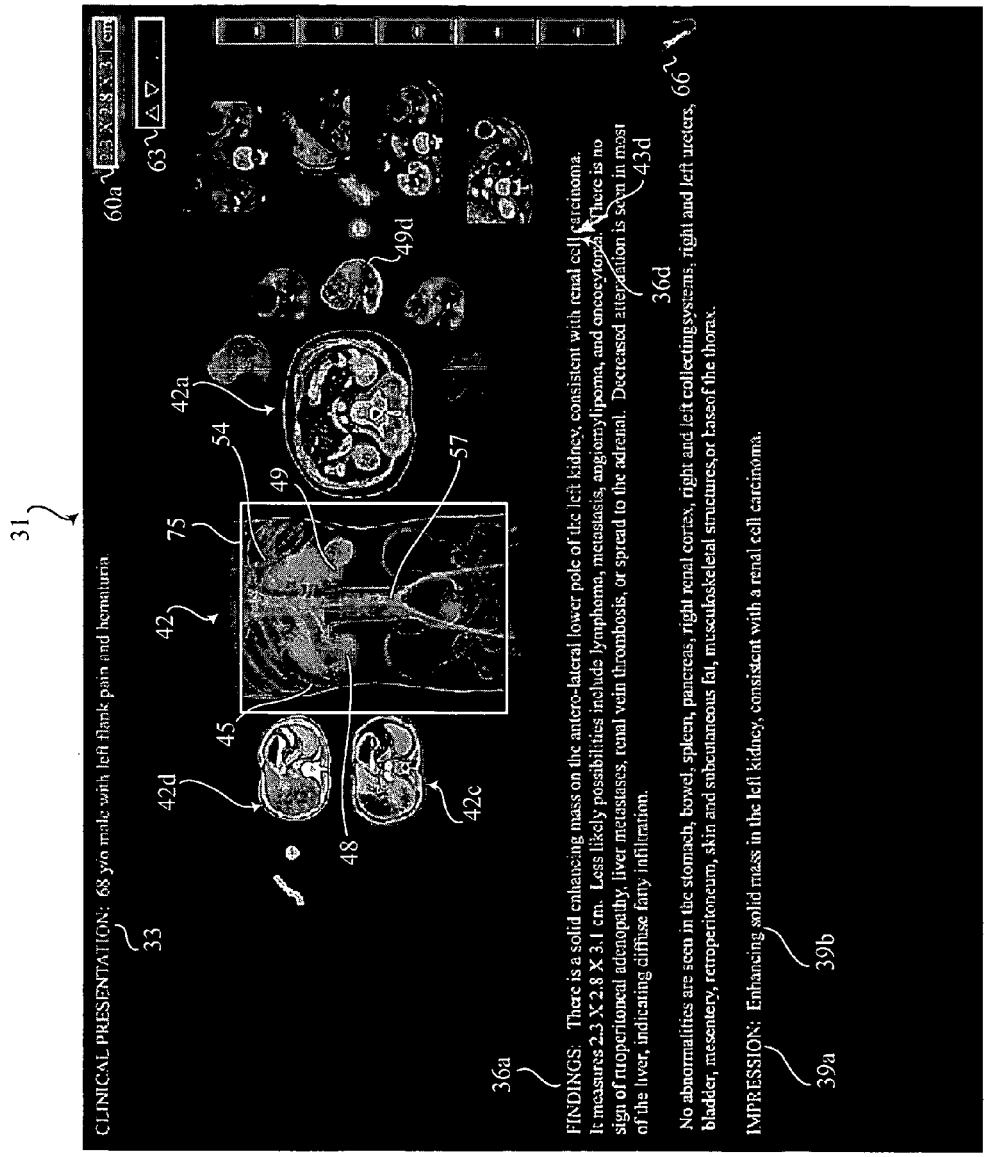
FIG. 10 is a ninth exemplary screen of showing formation of a report of radiological findings.

Referring to FIG. 10, knowing what a radiologist has not reviewed is as important as knowing what the radiologist has reviewed. The drawings 42 can be suitably truncated to indicate the area that has been visualized in the medical imaging examination.

A configurable pane 75 overlays the drawing 42 for the purpose of defining an outer limit of the radiologist's study. The configurable pane 75 will suitably truncate the drawing 42 that will accompany the textual report of findings 36*a* such that only that portion of the body that the radiological study includes, will be portrayed graphically in the drawing 42. The radiologist may readily configure the pane 75, in one embodiment, by dragging the lateral, top, and bottom sides of the configurable pane 75 to suitably truncate or expand the drawing 42, thereby conforming the drawing 42 to illustrate the portions of the anatomy the medical image included for evaluation.

Figure 12:
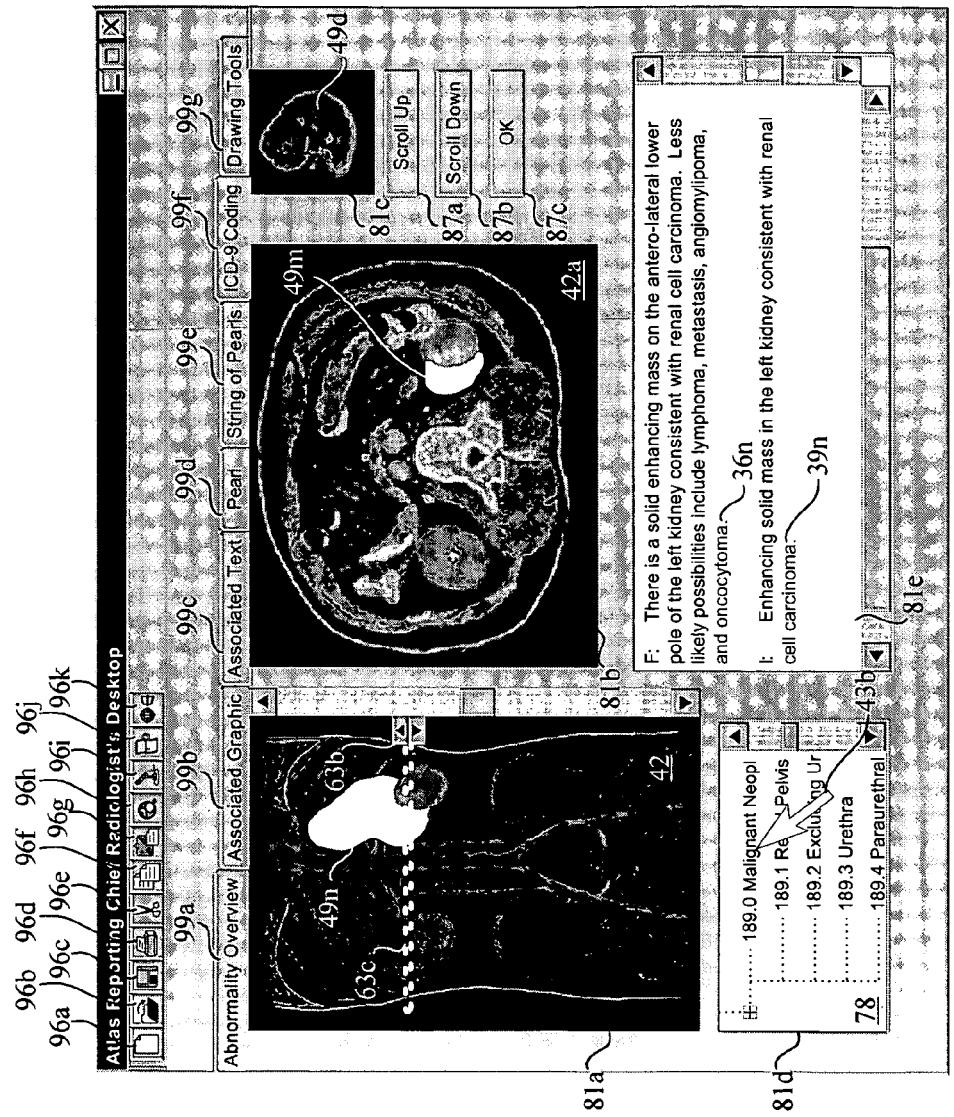
FIG. 12 is a first exemplary screen of a desktop application used to populate a database.

The discussion of the inventive system, method, and software has been directed at use. Referring to FIG. 12, the database is suitably constructed with associations to allow for the suitable retrieval of graphic and textual information in response to such indicator selections, keyboard inputs, verbal instructions, or other interactions with the database as the radiologist might have. Constructing the database, however, is accomplished by any suitable means. One such means is set out in the description of a Chief Radiologist's Desktop.

In one embodiment of the invention, the Chief Radiologists Desktop is configured to allow ready associations between implicated organs and structures and the graphical or textual information suitably stored in the system to facilitate the production of a radiologist's report. In an embodiment of the invention the database is configured with default associations that may be amplified, amended, or added to the database to allow advantageous interaction with the database. Thus, in the event of an adopted protocol at a hospital or clinic requiring a particular textual description or the inclusion of specific amplifying information, the Chief Radiologist's Desktop facilitates suitable editing of the database.

To use the Chief Radiologist's desk top, a Chief Radiologist will either create a new association with the new file button 96*a* or open an existing association with the open button 96*b*. For creating text, known editing commands are enabled in buttons such as the print button 96*d*, the save button 96*e*, the "cut" button 96*e*, the "copy" button 96*f*, the "paste" button 96*g*. Additionally, a search button 96*h* allows review of associations already created according to textual criteria. Three additional buttons exist. The microphone button 96*i* allows for voice recognition dictation of text, the keyword button allows for designation of keywords within the textual description by highlighting and clicking on the keyword. A zoom button 96*k* allows for close examination of a drawing 42 in order to specifically select an organ, structure, or location in the body.

In an "Abnormality Overview" tab 99*a*, the Chief Radiologist will activate the new button 96*a* to create a new association. In the case of organs with the torso, a coronal drawing 42 is presented representing the torso is place in the display box in response to the activation of the new button 96*a*. For the example of the left kidney, the Chief Radiologist will select a suitably cross-sectional drawing 42*a* using the torso drawing 42 and moving a cross-section locating line 63*c* by suitably engaging the cross-section selection aid 63*b* to a spot where the cross-section 42*a* includes a cross-section of the left kidney 49*m*. "Clicking" on the cross-section of the left kidney 49*m* highlights it in both the cross-sectional drawing 42*a* and in the coronal drawing 42 including a coronal view of the left kidney 49*n* present in the torso drawing 42.

In a presently preferred embodiment, the three-dimensional anatomical model (not shown) exists in the database. The three dimensional model includes a complete human body comprising spatial modeling of each organ or structure the body comprises. In alternate embodiments, the anatomic model includes additional models necessary for complete depiction of all internal structures. Such depictions include both male and female depictions of infant, adolescent, and mature human anatomy.

A voxel is a unit of graphic information that defines a point in 3 dimensional space. Since a pixel (picture element) defines a point in three-dimensional space with its x and y coordinates, a third z coordinate is needed. In 3-D space, each of the coordinates is defined in terms of its position, where any point or group of points is expressed with a range of x-, y-, z coordinates that define a location within a body model and allows that point to be associated with data. Much of the medical imagery discussed above use images defined by voxels and suitable software to view sonograms, computer tomography (CT), and magnetic resonance imaging (MRI) scans from different angles, effectively to visualize and analyze tissues and organs inside of the body without surgical dissection. The anatomic model is defined by a number of voxels, each suitably assigned to an organ or structure within the body, when taken in aggregate, define the whole of the body.

As the basic associative link between spatial and symbolic knowledge, a lower level consists of one or more discrete data volumes, as obtained from computed tomography (CT), magnetic resonance imaging (MRI), or other imaging sources. A set of attributes is assigned to every voxel, indicating its membership to anatomical regions. These object labels are stored in one or more label volumes. The lower level is thus equivalent to the previously described generalized voxel model.

Referring to FIG. 12, as a consequence of the space-filling anatomic model, the contents of the knowledge base may be accessed at any point of a 3D image. Symbolic descriptions may thus be obtained by simply clicking on an image. When a voxel depiction of a torso drawing 42 of the anatomic model is presented in a pane 81*a* to represent the "visible man," a cross-section selection aid 63*b* and cross-section locating line 63*c*, are included to allow a radiologist to select a cross-section for view. Selecting a cross-section 42*a* for view allows the selection of a particular organ or structure where the organ or structure may overlap another in the torso drawing 42. A cross-section 42*a* of the torso drawing 42 appears in a second pane 81*b* corresponding to the location of the cross-section locating line 63*c* on the torso drawing 42.

Because the voxel having the coronal height (z) determined by the cross-section locating line, and the x and y coordinates set forth in the selected cross-section, corresponds to the left kidney, a simple search of the voxels for all of those corresponding to the left kidney makes possible a three-dimensional rendering of the left kidney in both the coronal view of the torso drawing 42 and the cross-sectional view 42 a of the torso. Having selected the left kidney, all graphics depicting the left kidney shall be available in an organ or structure pane 81*c*. Certain tissue properties detected by medical exams in organs or abnormalities may help the interpreting radiologist suggest a probable diagnosis or at least limit the differential list of diagnoses. An example is a renal mass with contrast enhancement on CT indicating a blood supply suggesting a renal carcinoma. If fat is also detected within the voxels of the mass (low density tissue −50 to −100 HU), then mass is benign and the study is diagnostic of a renal hamartoma called an angiomyolipoma. When an embodiment retrieves data associated with a selected tissue voxel from the medical exam and matches it with the anatomic location on the retrieved drawing the radiologist can improve the specificity of his analysis of the exam.

Each of the associated graphics, such as the renal cell carcinoma graphic 49*d* then associated with the left kidney are then available for viewing in the organ or structure pane 81*c*. In one embodiment, selection of one of the associated graphics such as the renal cell carcinoma kidney cross-section 49*d*, will allow an ICD-10 coding 78 to appear in a coding pane 81*d* and a suitably designated impression 36*n* and finding 39*n* to appear in the narrative pane 81*e*. Each of the coding 78, and the impression 36*n* and finding 39*n* associated with the renal cell carcinoma kidney cross-section 49*d*, may be edited by moving the indicator 43*b* to a suitable code and then clicking "OK" 87*c*. Alternatively, a distinct page and tab is dedicated to associating, in the case of codes, the "ICD-10 Coding" tab 99*f*, and in the case of findings 36*n* and impressions 39*n*, the "Associated Text" tab 99*c*. Thus, for each observed phenomenon relating to the selected organ or structure, the database can suitably expand with associations to facilitate inclusion of each despicable graphic.

A "Drawing Tools" tab 99*g* is included to allow a radiologist to create suitable graphics for depiction of particular abnormalities. The drawing tools are used to form a palette that is used to create abnormalities within the anatomic model. Thus, where a Chief Radiologist wishes to portray a renal cell carcinoma which has a distinctive return in a CT scan, the radiologist may invoke the textures and shades normally associated with renal cell carcinoma to generate a representative drawing by means of drawing tools. Using these in conjunction with the model, voxel by voxel placement of an abnormality within a left kidney cross-section or any other organ or structure is possible for association with any organ or structure in the model.

Figure 13:
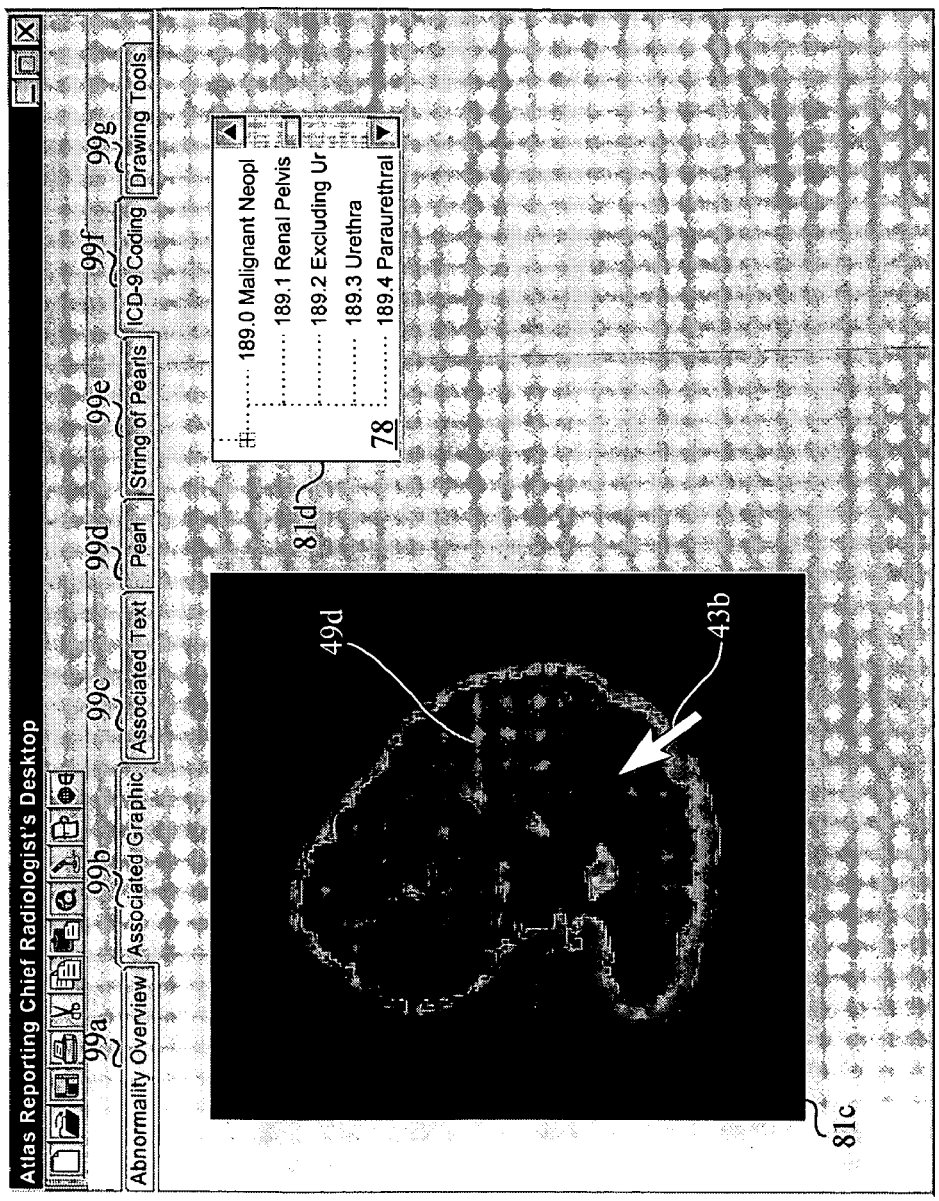
FIG. 13 is a second exemplary screen of a desktop application used to populate a database.

Referring to FIGS. 12 and 13, in order, then to create the proper associations, between the produced drawing 81*c* and the ICD-10 coding and the newly created drawing, the radiologist will activate Tab 99*f*, and in the coding pane 81*d*, will select the appropriate morbidity code 78 and click on the drawing 49*d* with the indicator 43*b* to create the association in the database. Consequently, the drawing 49*d* and the ICD-10 coding 81*d* appear in the respective panes 81*c* and 81*d* of the "Abnormality Overview" tab 99*a*.

Using the "Associated Text" tab in a similar manner allows the radiologist to create the association of a textual block with the graphic.

Figure 14:
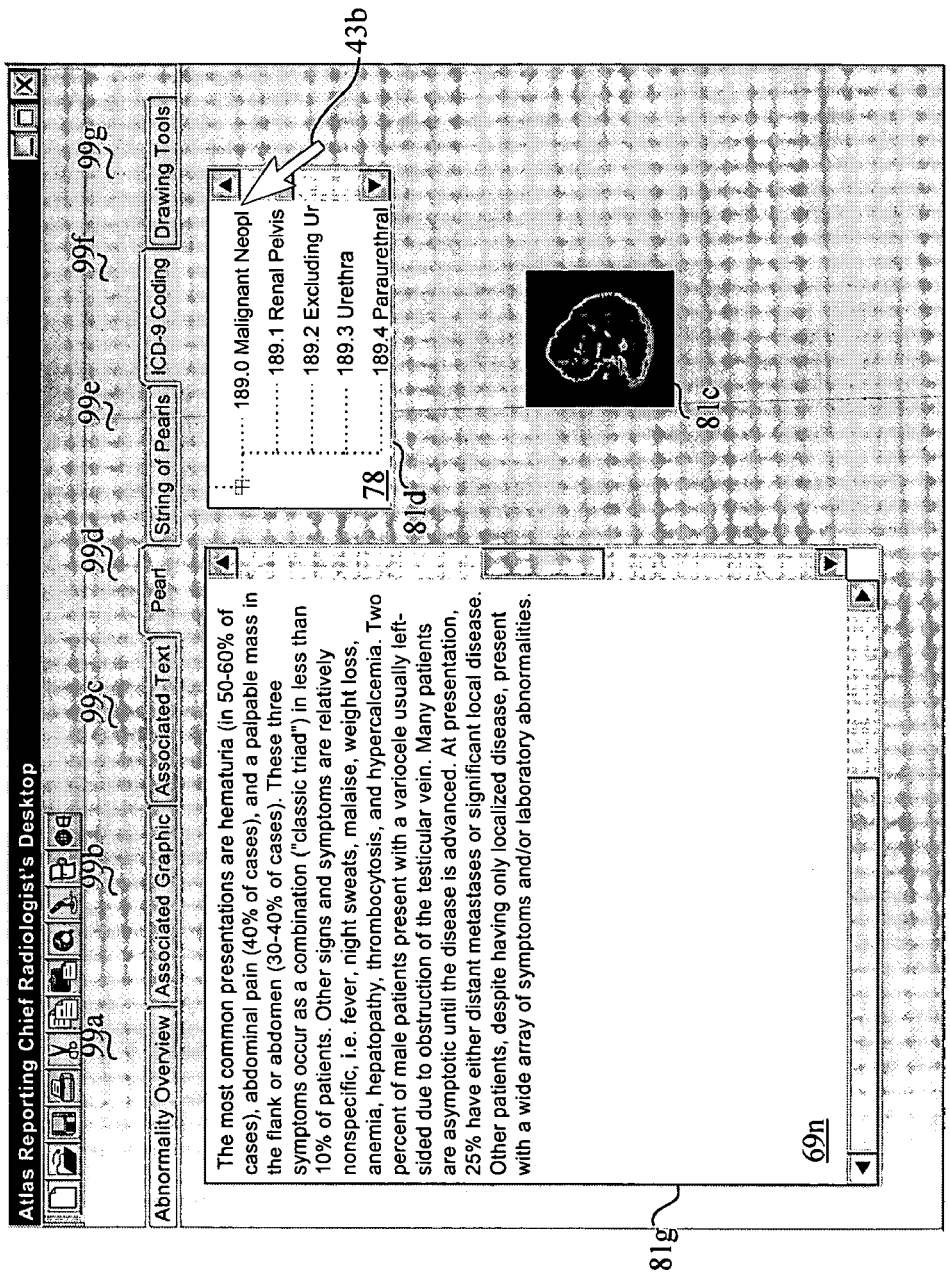
FIG. 14 is a third exemplary screen of a desktop application used to populate a database.

Referring to FIG. 14, a pearl is generated by clicking on the "Pearl" tab 99*d*. In the illustrated embodiment, the ICD-10 coding 78 appears in the pane 81*d* as well as the drawing 49*d* in the pane 81*c* to aid the Chief Radiologist in crafting the "pearl." The Chief Radiologist now can use the pane 81*g* to draft the pearl 69*n*.

Figure 15:
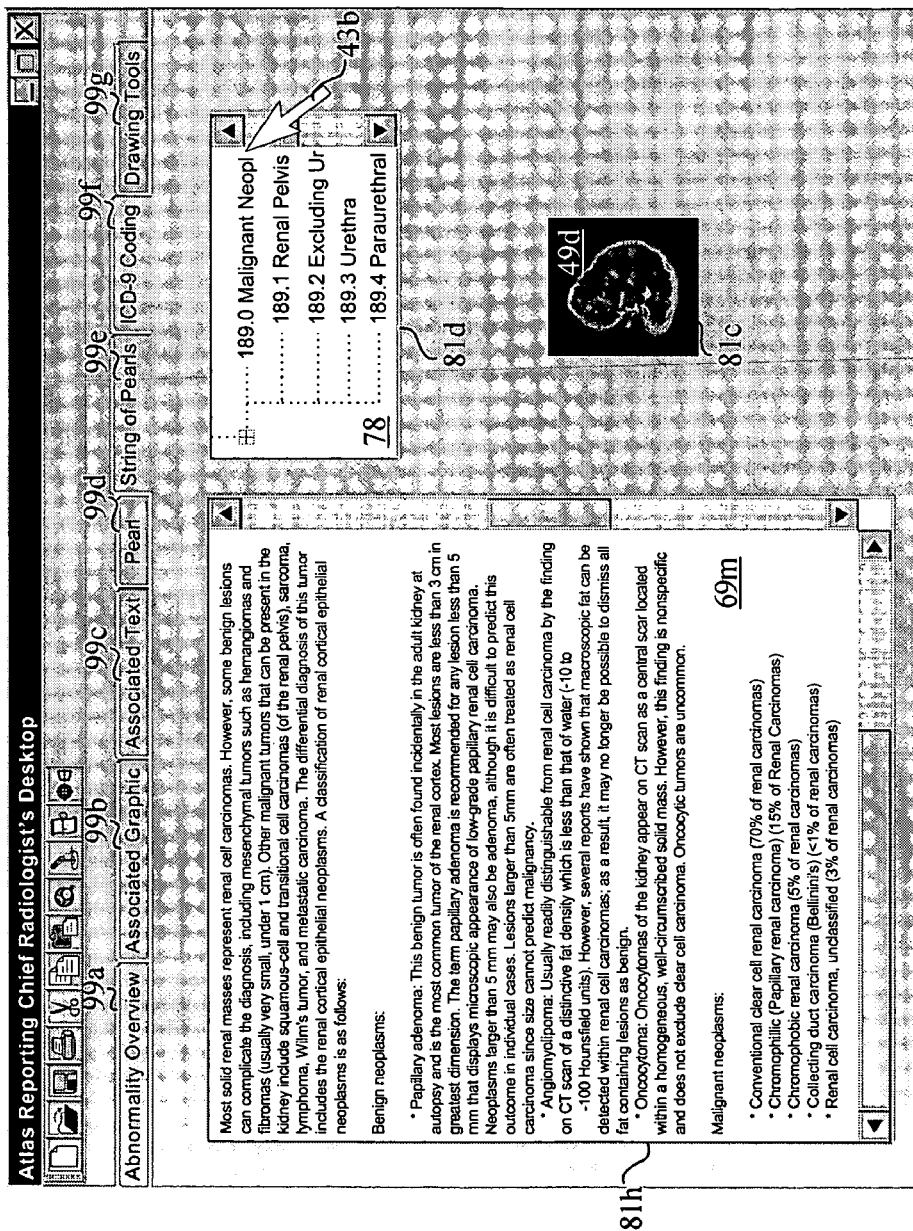
FIG. 15 is a fourth exemplary screen of a desktop application used to populate a database.

Referring to FIG. 15, the "String of Pearls" tab allows the association of text for the "string of pearls" 69*m* is similarly generated in the pane 81*h* associated with the drawing 49*d* appearing in the pane 81*c*.

Object names appear on a pop-up menu, together with the names of the objects they are related to. By selecting a name, objects may automatically be annotated, painted, added or removed, or additional texts and other information may be requested.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method for generating a report of findings from a medical image, the method comprising:
   under control of a computing system,
   displaying a medical image including an anatomic structure; retrieving a plurality of idealized drawings associated with the anatomic structure; the idealized drawings configured to each graphically represent a distinct anatomic abnormality;
   receiving a signal indicative of a radiologist of clicking on one drawing from the plurality of drawings; and
   retrieving drawing data associated with the one drawing, the drawing data configured for inclusion in the report of findings.

2. The method of claim 1, wherein selecting an anatomic structure is according at least one factor from a group of factors, the group consisting of clinical presentation, indicia present in the medical image, based upon examination orders, preliminary diagnosis, and previous examination.

3. The method of claim 1 wherein the receiving a medical image including an anatomic structure includes clicking on a picture element in a medical illustration, the picture element being associated with the anatomic structure.

4. The method of claim 3, wherein the picture element is configured to graphically represent the anatomic structure.

5. The method of claim 1, wherein the receiving a medical image including an anatomic structure includes locating, on a display device a configurable pane in a graphic user interface a truncation of the medical image.

6. The method of claim 1, wherein retrieving drawing data includes retrieving text data for inclusion in the report.

7. The method of claim 6, wherein the text data includes a textual from a textual template group, the textual template group consisting of diagnoses, prognoses, treatment suggestions, additional differential testing, and implicated structures findings, impressions, suggested treatment, follow-up examination regimen, and morbidity coding.

8. The method of claim 6, wherein the text data includes a billing coding associated with the drawing.

9. The method of claim 8, wherein the inclusion is selected from the group including a cyst, a polyp, a tumor, a lesion, a wart, a mole, a scar, and a clot.

10. The method of claim 1, wherein the anatomic abnormality includes at least one of a group of structure abnormalities, the group consisting of size of the at least one structure, texture of the at least one structure; and an abnormal boundary of the at least one structure.

11. The method of claim 1, wherein the anatomic abnormality includes an inclusion.

12. The method of claim 1, wherein the anatomic abnormality includes a fracture.

13. The method of claim 1, wherein receiving a medical image including the anatomic structure is according to a keyword.

14. The method of claim 13, wherein the keyword is recognized by voice recognition software.

15. The method of claim 1, wherein selecting receiving a medical image including the anatomic structure includes highlighting a medical illustration according to the selected anatomic structure.

16. The method of claim 1, further comprising augmenting the report with amplifying data.

17. The method of claim 16, wherein the amplifying data includes data selected from an amplifying group consisting of textual excerpts of medical history, graphical excerpts of the medical image, and graphical excerpts from previous medical images.

18. The method of claim 16, wherein amplifying data includes textural negative findings based upon a content of the medical image.

* * * * *